United States Patent [19]

Pittet et al.

[11] Patent Number: 4,565,707
[45] Date of Patent: Jan. 21, 1986

[54] FLAVORING WITH DIALKYLTHIOALKENES, DIALKYLTHIOALKYLCYCLOALKENES AND MONOALKYLTHIOALKENYLCYCLOALKENES

[75] Inventors: Alan O. Pittet, Atlantic Highlands; Ranya Muralidhara, Fair Haven; Kevin P. Miller, Middletown; Domenick Luccarelli, Jr., Neptune; Manfred H. Vock, Locust, all of N.J.

[73] Assignee: International Flavors & Fragrances Inc., New York, N.Y.

[21] Appl. No.: 731,919

[22] Filed: May 8, 1985

[51] Int. Cl.$^4$ .................. A23L 1/226; A23L 1/231; A23L 1/235
[52] U.S. Cl. .................. 426/535; 568/57; 568/39; 568/59
[58] Field of Search .................. 426/535; 568/57

[56] References Cited

U.S. PATENT DOCUMENTS 4,481,224 11/1984 Muralidhara et al. .......... 426/535
4,493,852 1/1985 Zauno et al. .................. 426/535
4,504,508 3/1985 Pittet et al. .................. 426/535

OTHER PUBLICATIONS

Chemical Abstracts: 97(11):91694w, (1982).
Boelens et al., Organic Sulfur Compounds from Fatty Aldehydes, Hydrogen Sulfide, Thiols and Ammonia as Flavor Constituents, J. Agr. Food Chem., vol. 22, No. 6, 1974, pp. 1071–1076.

Primary Examiner—Joseph Golian
Attorney, Agent, or Firm—Arthur L. Liberman

[57] ABSTRACT

Described are dialkylthioalkenes, dialkylthioalkylcycloalkenes and monoalkylthioalkenylcycloalkenes defined according to the generic structure:

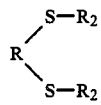

as well as the genus defined according to the structure:

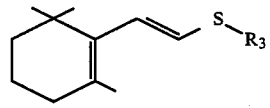

wherein R represents $C_6$–$C_{11}$ alkenyl or cycloalkenylalkyl; and wherein $R_2$ represents $C_1$–$C_3$ alkyl and $R_3$ is $C_1$–$C_3$ alkyl and organoleptic uses thereof in augmenting or enhancing the aroma or taste of foodstuffs, chewing gums, toothpastes or medicinal products.

2 Claims, 17 Drawing Figures

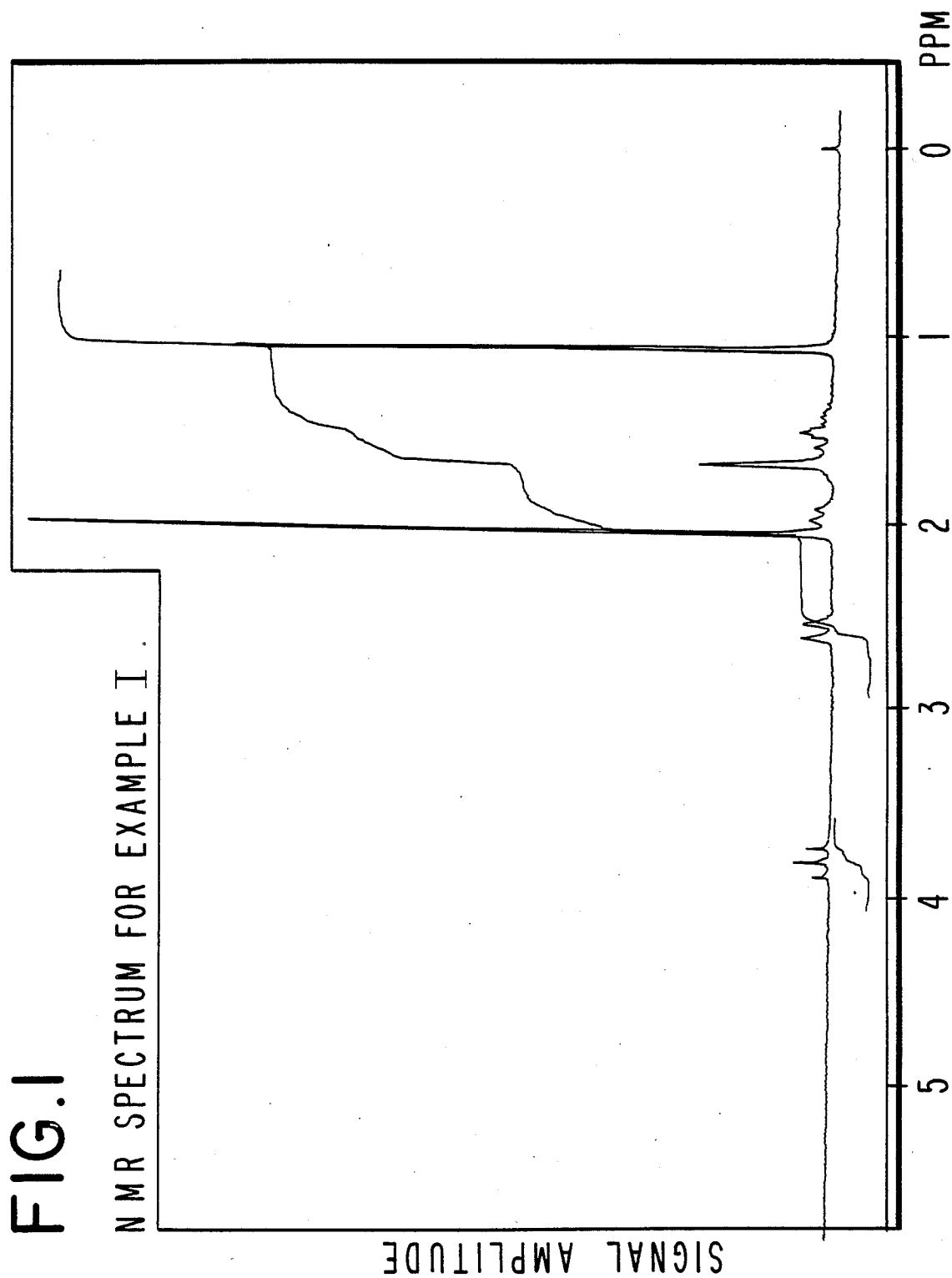
FIG.1 NMR SPECTRUM FOR EXAMPLE I

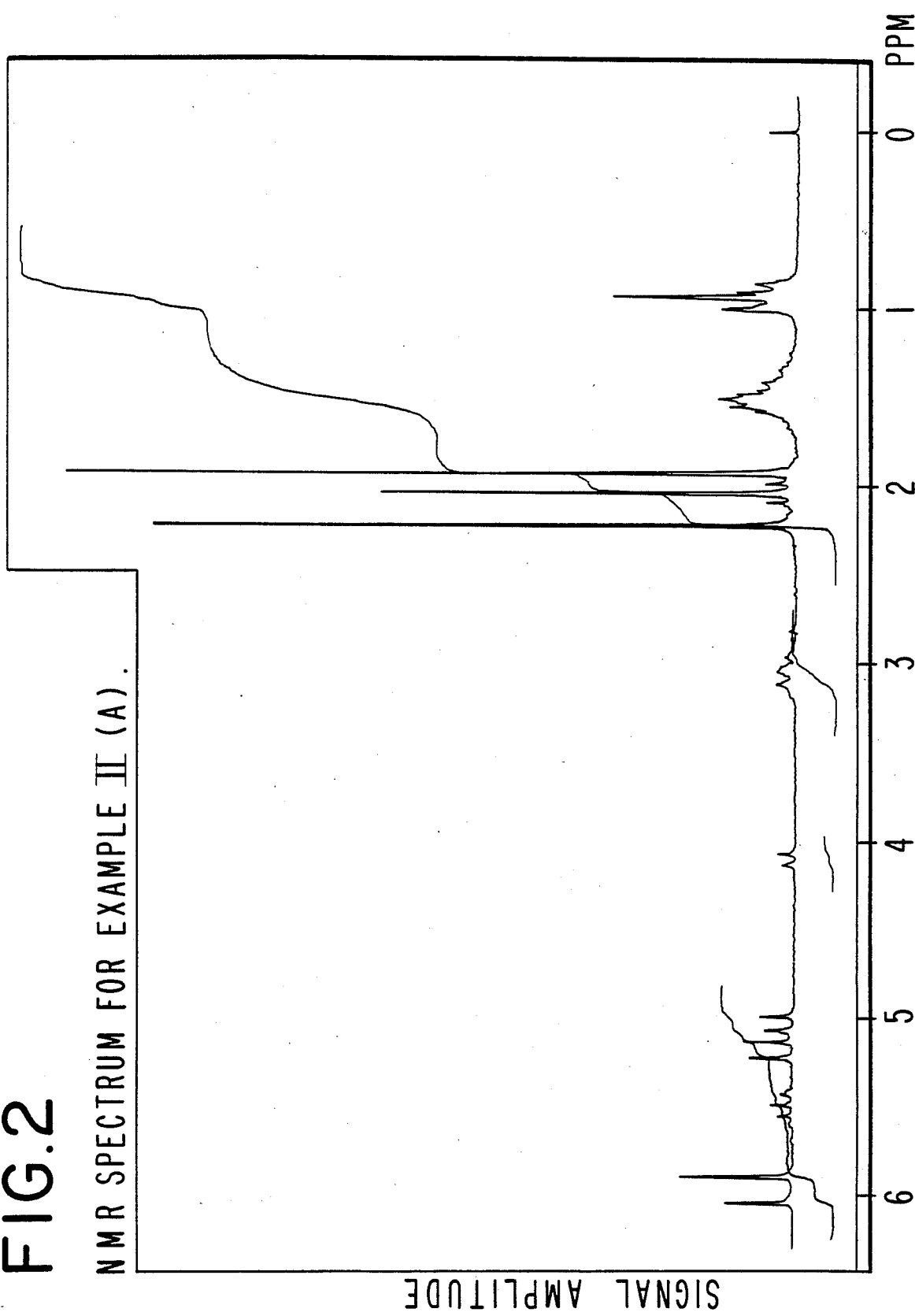
FIG. 2 NMR SPECTRUM FOR EXAMPLE II (A)

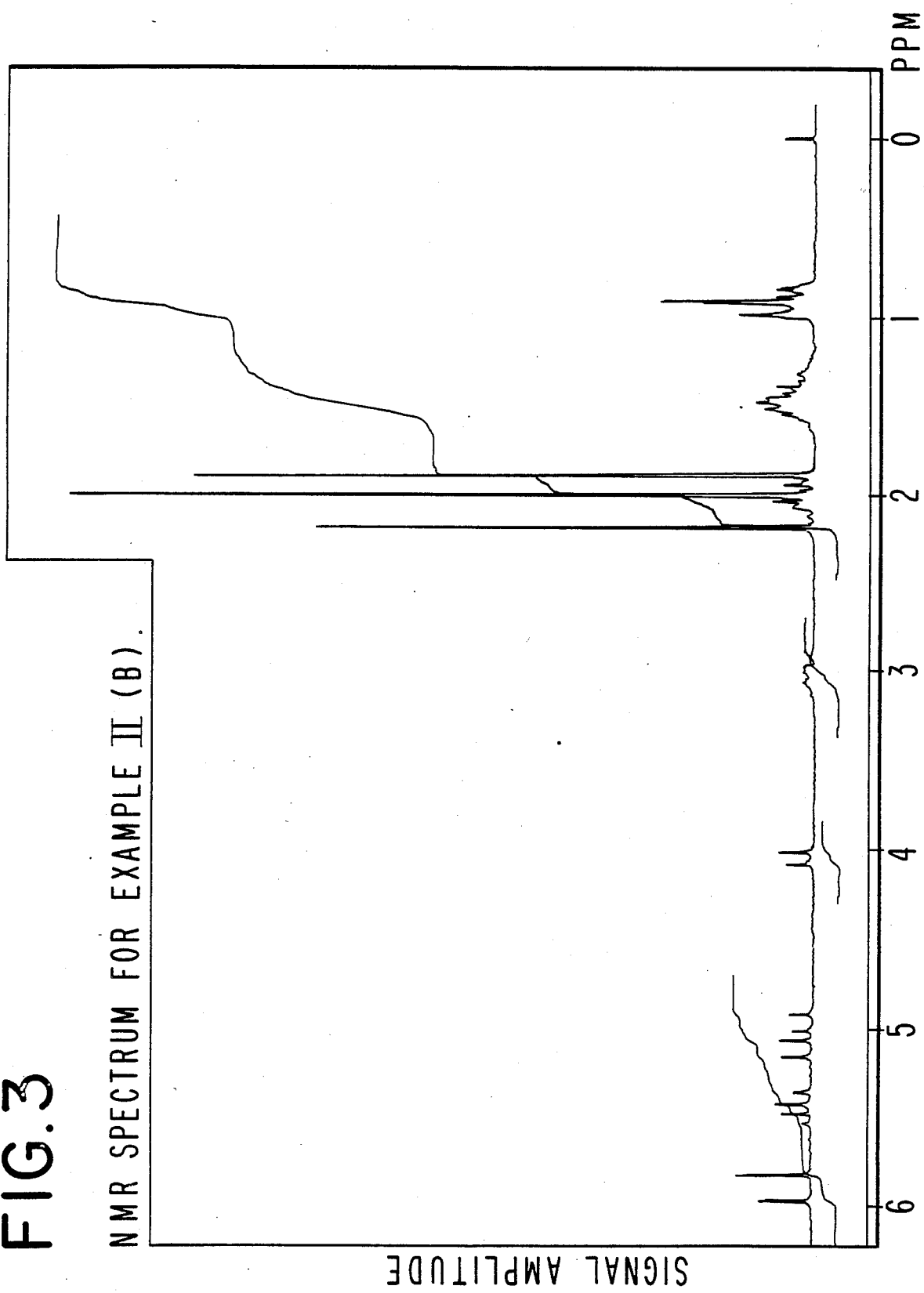

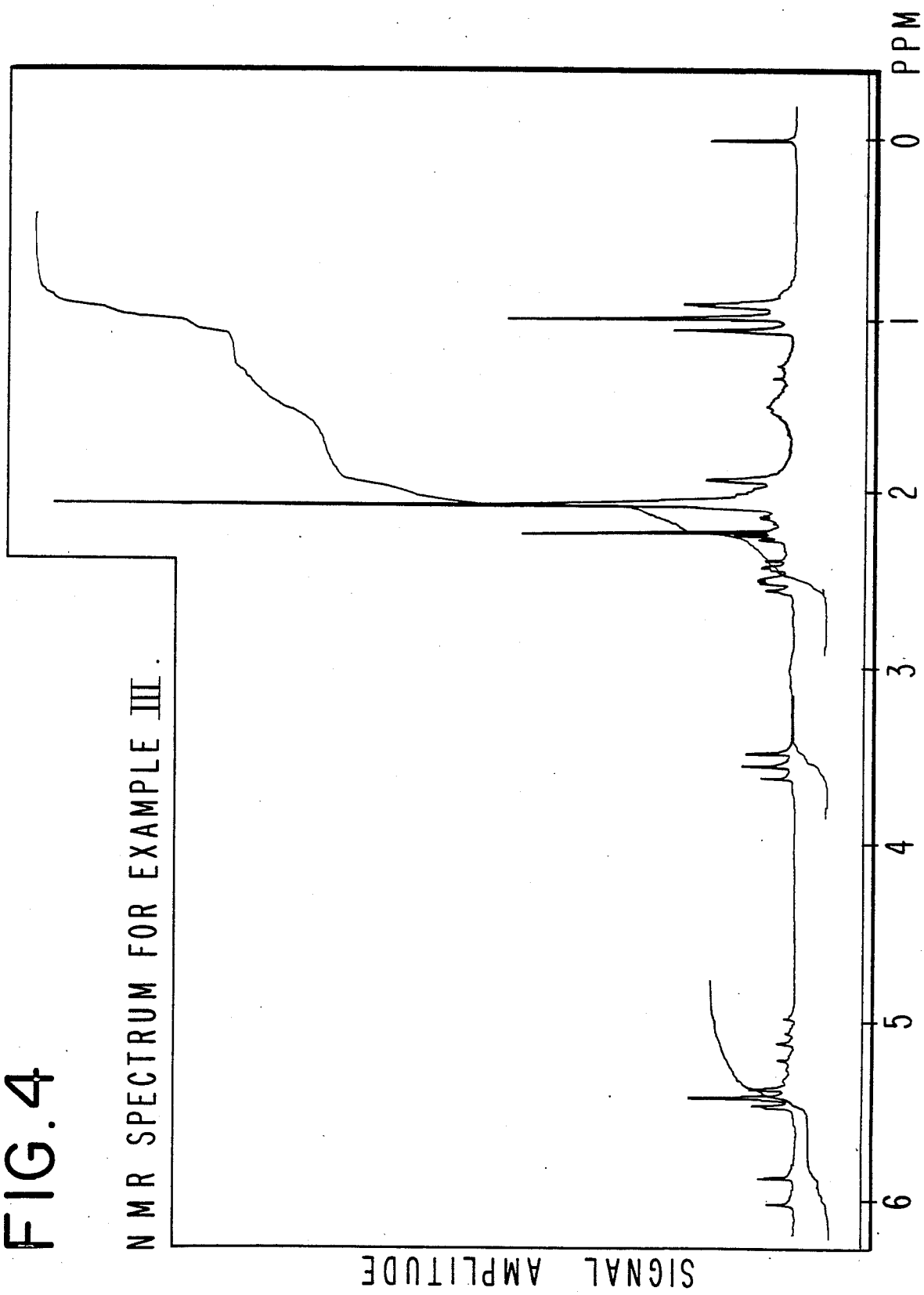
FIG. 4 NMR SPECTRUM FOR EXAMPLE III.

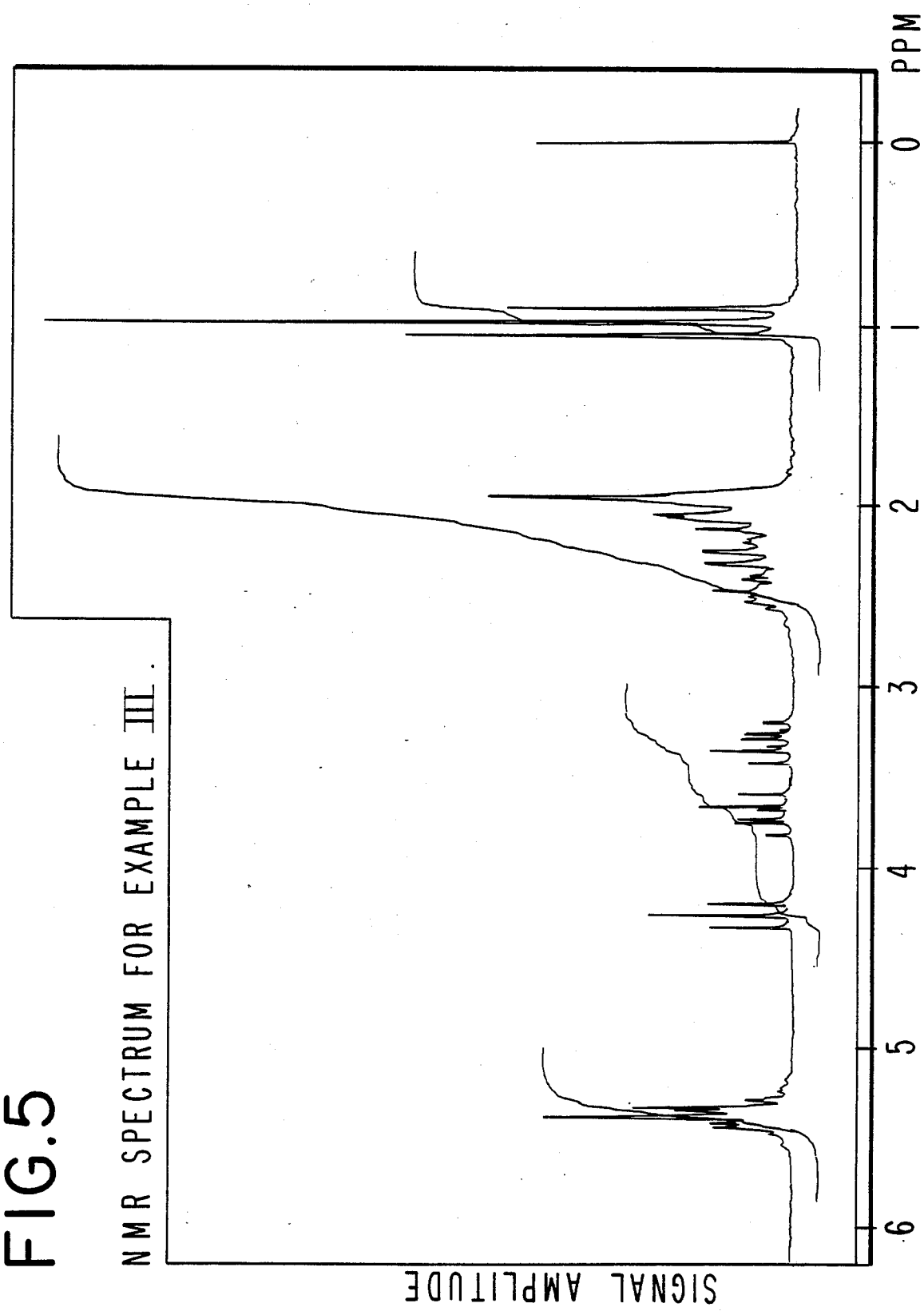
FIG. 5 NMR SPECTRUM FOR EXAMPLE III.

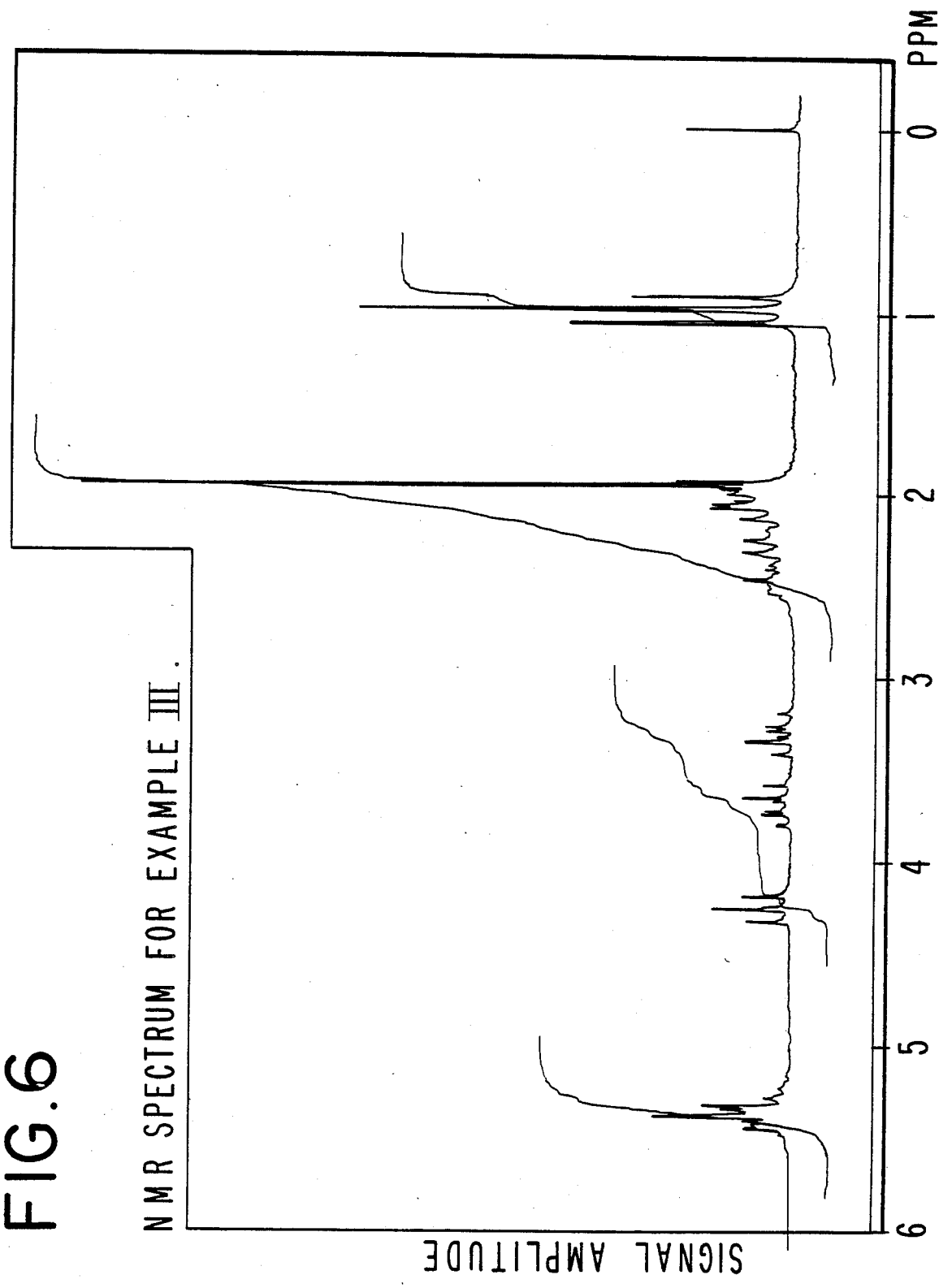
FIG. 6 NMR SPECTRUM FOR EXAMPLE III.

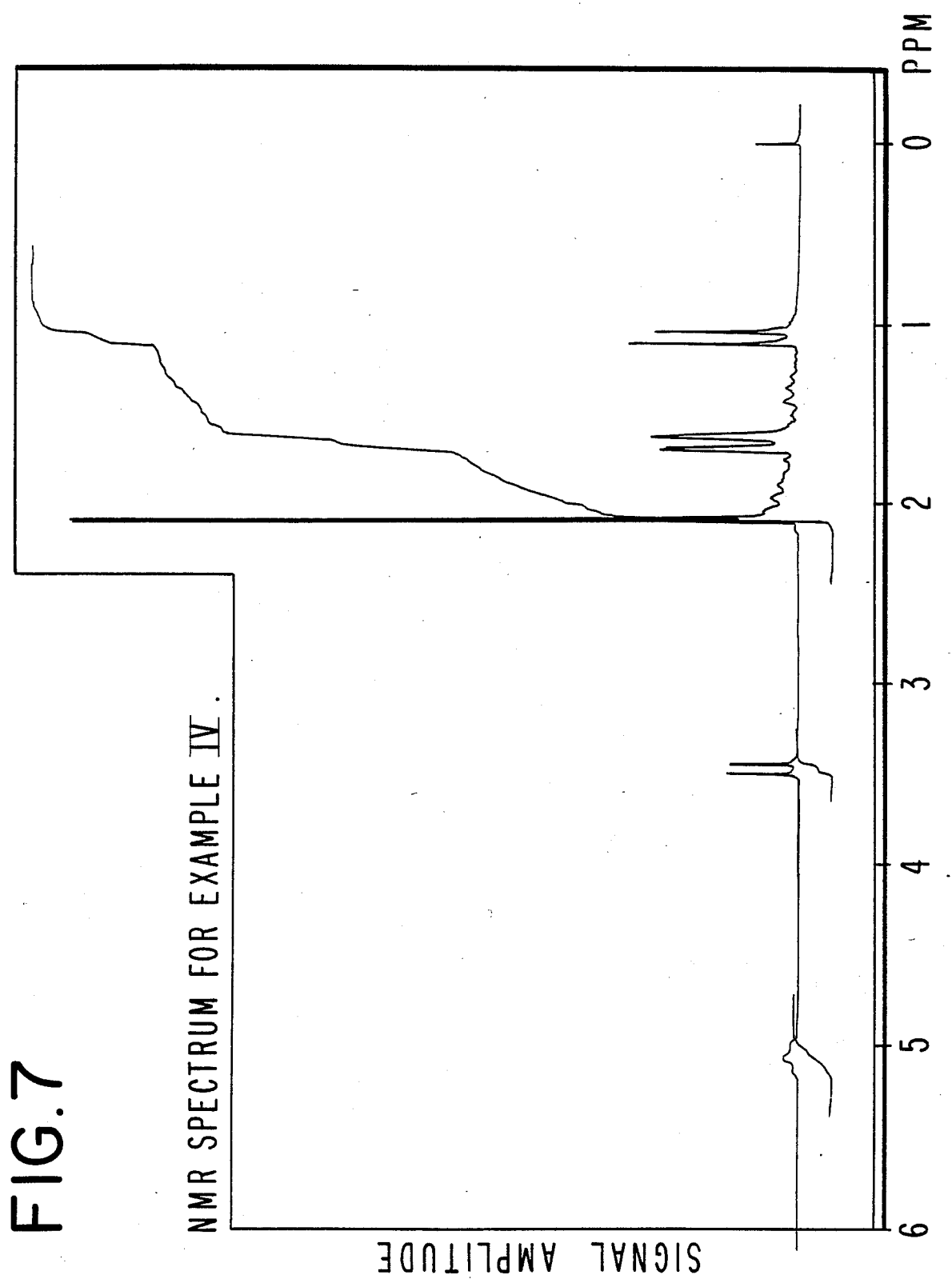
FIG. 7 NMR SPECTRUM FOR EXAMPLE IV.

GLC PROFILE FOR EXAMPLE XVII CRUDE

GLC PROFILE FOR EXAMPLE XVI CRUDE

FIG. 9 NMR SPECTRUM FOR EXAMPLE XVI, PEAK 81 OF FIG. 8.

NMR SPECTRUM FOR EXAMPLE XVI, PEAK 82 OF FIG. 8.

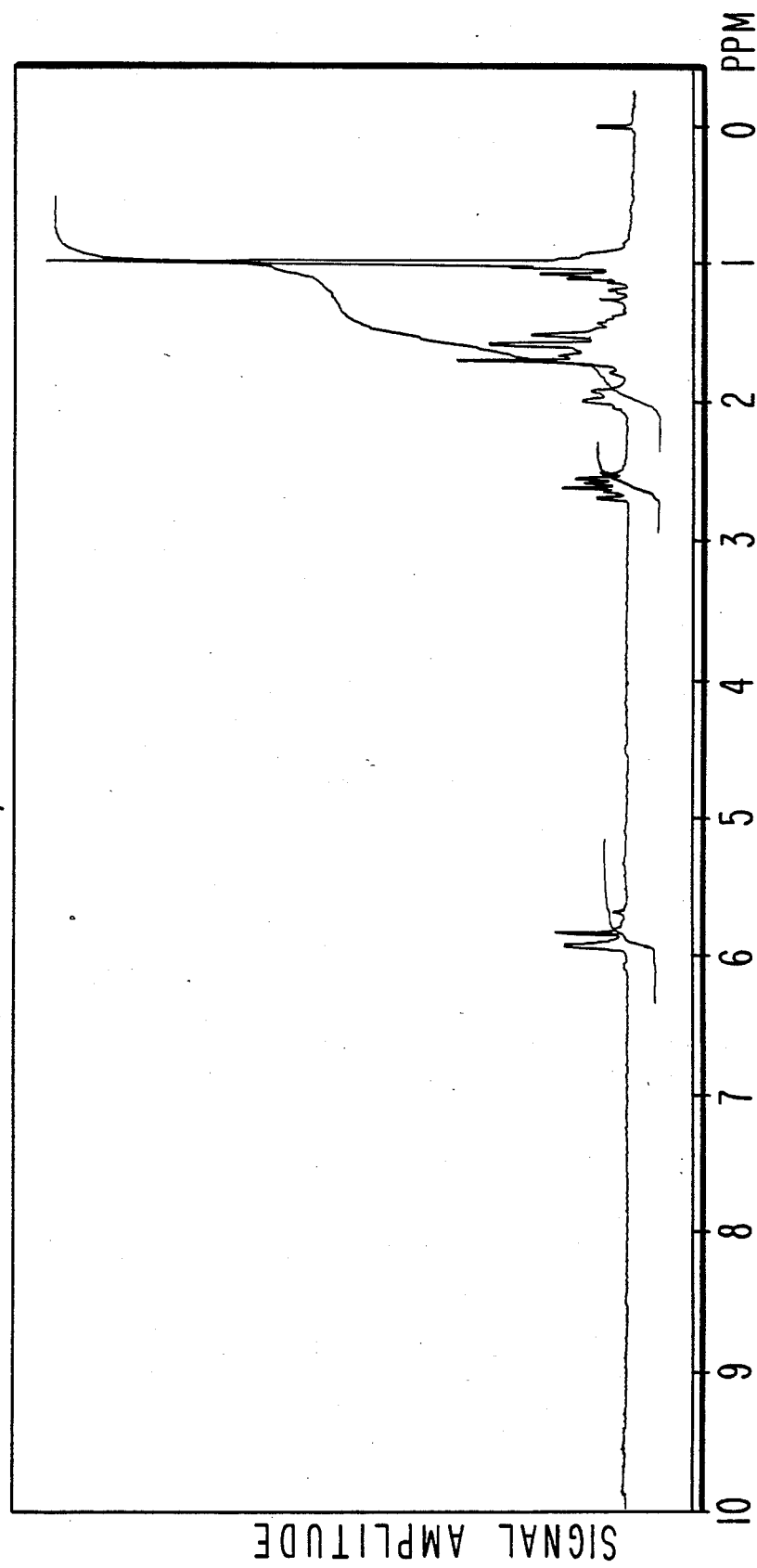

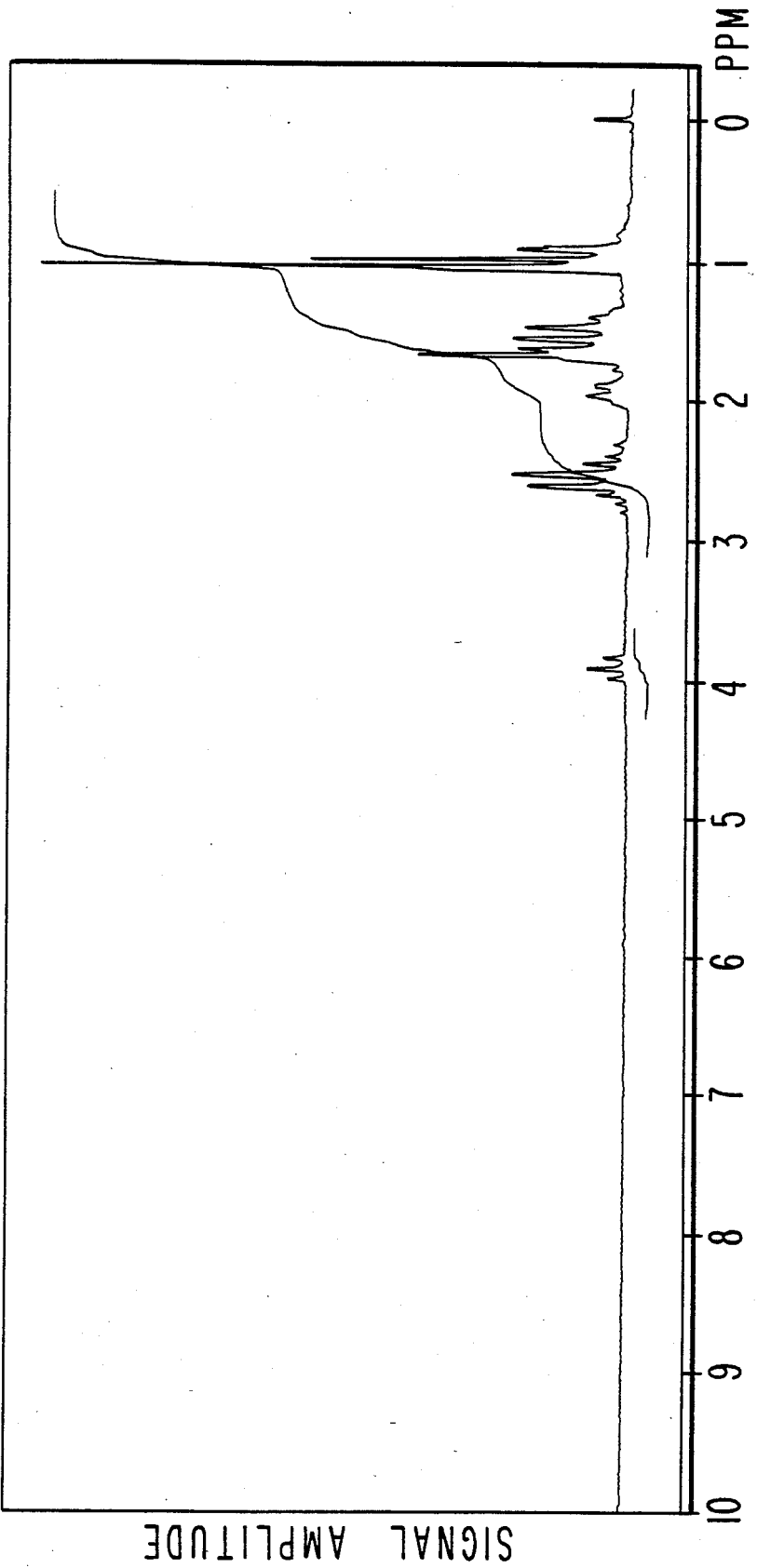
FIG.13 NMR SPECTRUM FOR EXAMPLE XVII, PEAK 112 OF FIG.II.

GLC PROFILE FOR EXAMPLE XXI
CRUDE

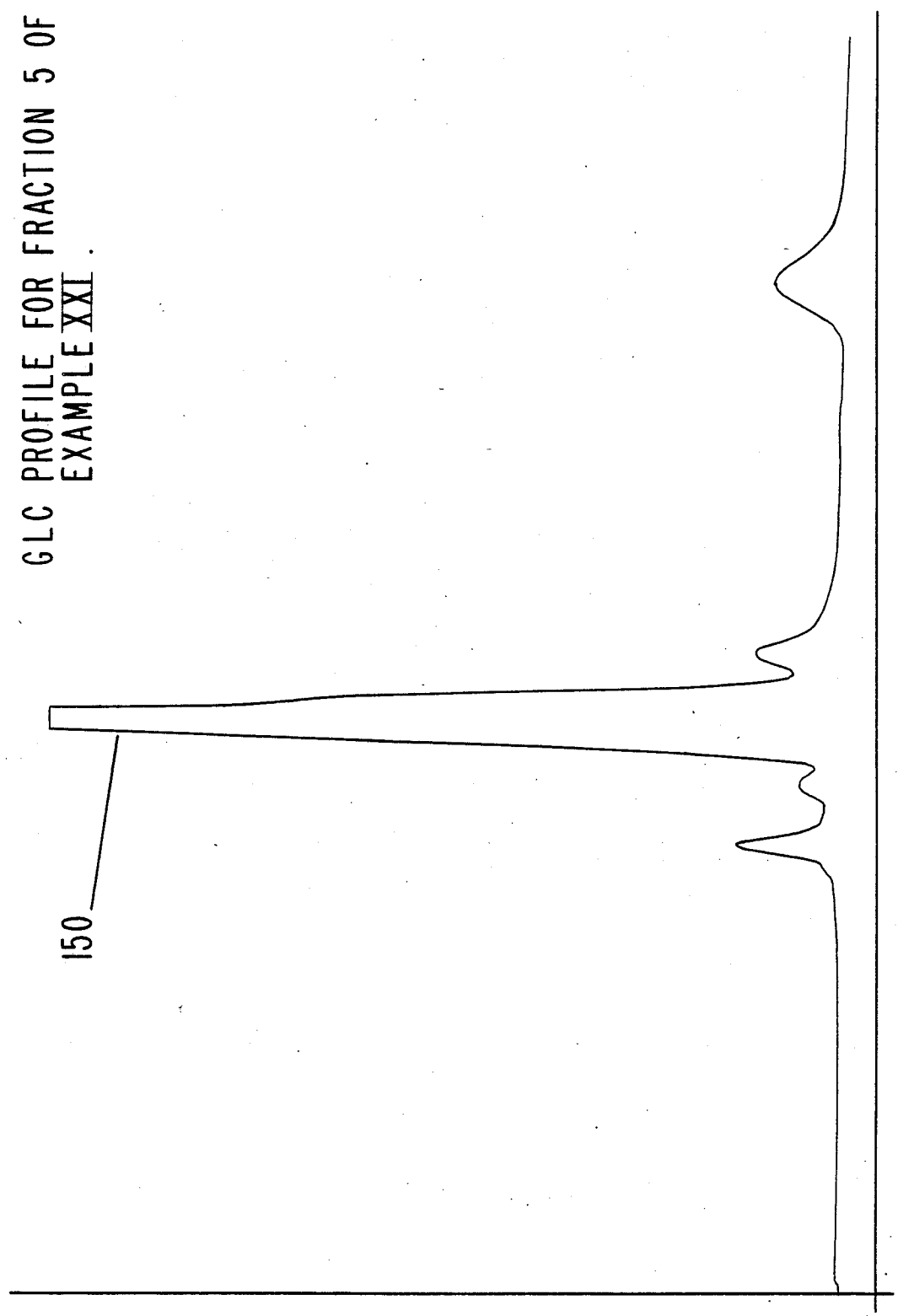

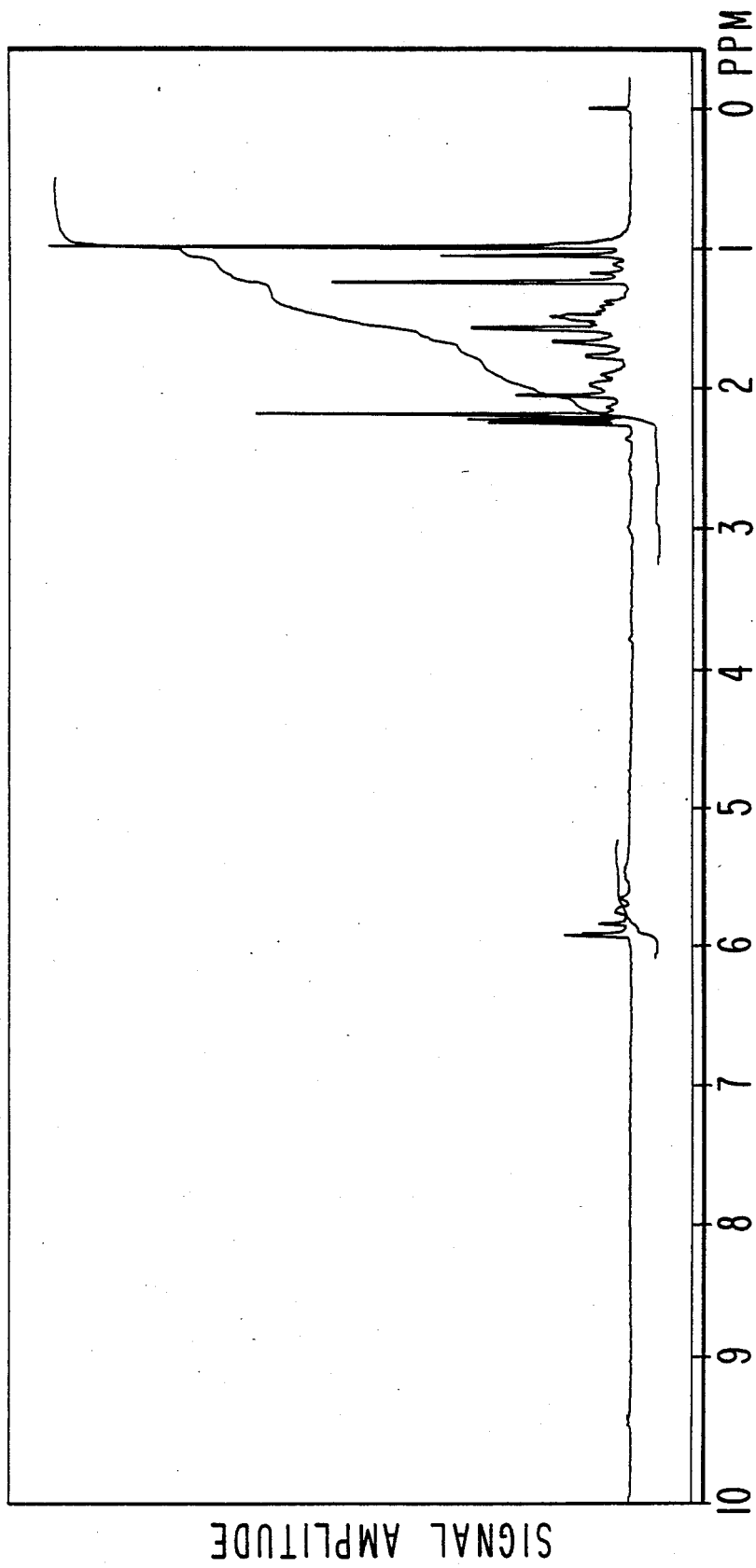
FIG. 16 NMR SPECTRUM FOR EXAMPLE XXI, FRACTION 5.

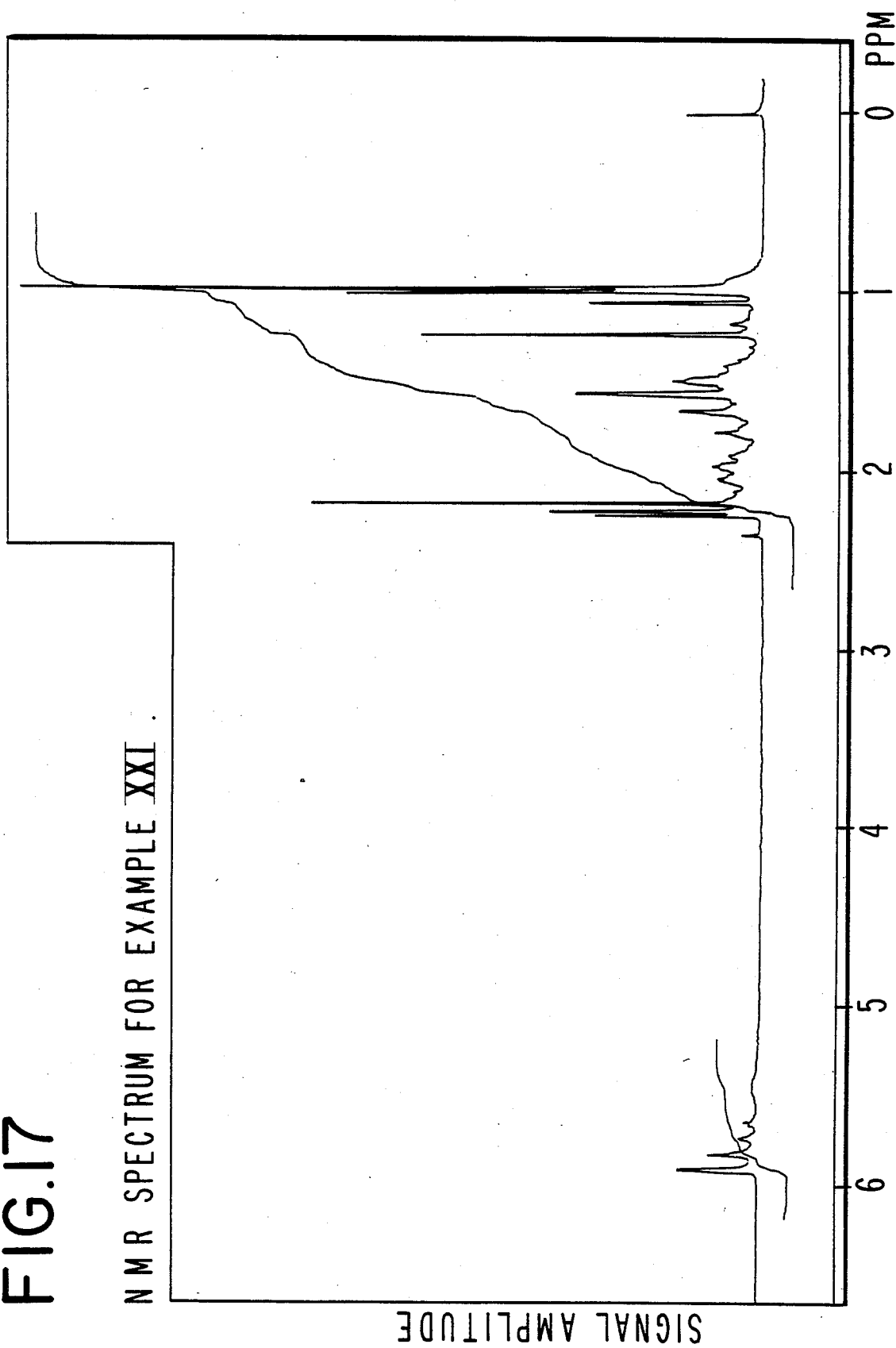
FIG.17 NMR SPECTRUM FOR EXAMPLE XXI

FLAVORING WITH DIALKYLTHIOALKENES, DIALKYLTHIOALKYLCYCLOALKENES AND MONOALKYLTHIOALKENYLCYCLOALKENES

BACKGROUND OF THE INVENTION

This invention describes dialkylthioalkenes, dialkylthioalkylcycloalkenes and monoalkylthioalkenylcycloalkenes defined according to the generic structure:

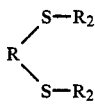

wherein R represents $C_6$–$C_{11}$ alkenyl or cycloalkenylalkyl; and $R_2$ represents $C_1$–$C_3$ alkyl and uses thereof in augmenting or enhancing the aroma or taste of foodstuffs, chewing gums, toothpastes and medicinal products.

Artificial flavoring agents for foodstuffs have received increasing attention in recent years. In many areas such food flavoring agents are preferred over natural flavoring agents at least in part because of the uniform flavor that may be so obtained. For example, natural food flavoring agents such as extracts, essences, concentrates and the like are often subject to wide variation due to changes in the quality, type and treatment of the raw materials. Such variation can be reflected in the end product and results in unreliable flavor characterists and uncertainty as to consumer acceptance and cost. Additionally, the presence of the natural product in the ultimate food may be undesirable because of the increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in preparing artificial flavoring agents is that of achieving as nearly as possible a true flavor reproduction. This generally proves to be a difficult task since the mechanism for flavoring development in many foods is not understood. This is notable in products having blueberry, blackcurrant, guava, grapefruit, tomato, garlic and hydrolyzed vegetable protein-like taste nuances.

Reproduction of blueberry, blackcurrent, vanilla, guava, grapefruit, galbanum, tomato, garlic, green, hydrolyzed vegetable protein-like, beany and cooked vegetable-like, fried onion, floral, roasted, onion, crisp roasted, bacon, sweet, cherry and marachino cherry-like aroma and taste naunces has been the subject of a long and continuous search by those engaged in the production of foodstuffs, chewing gums, toothpastes and medicinal products. The severe shortage of foods, especially protein foods, in many parts of the world has given rise to the need for utilizing non-meat sources of proteins and making such protein as palatable and as meat-like as possible. Hence, materials which will closely simulate or exactly reproduce the flavor or aroma of mushroom, hydrolyzed, vegetable protein and garlic are required. Furthermore, meat flavors have been enhanced previously by the use of such materials as monosodium glutamate. In many diets monosodium is not desired. Therefore, a need has arisen for a monosodium glutamate replacer.

Moreover, there are a great many of meat cotaining or meat based foods presently distributed in a preserved form. Examples of such substances are condensed soups, dry-soup mixes, dry meat, freeze-dried or lypophilized meats, packaged gravies and the like. While these products contain meat or meat extracts, the fragrance, taste and other organoleptic factors are very often impaired by the processing operation and it is desirable to supplement or enhance the flavors of these preserved foods with versatile materials which have hydrolyzed vegetable protein-like nuances as well as garlic and beany nuances.

U.S. Pat. No. 4,472,446 issued on Sept. 18, 1984 discloses methyl(methylthioalkyl)-1,3-dithiolanes defined according to the structure:

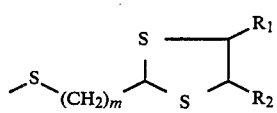

wherein $R_1$ and $R_2$ are the same or different and each represents methyl or hydrogen with the proviso that at least one of $R_1$ and $R_2$ is methyl; and wherein m represents an integer of 1 or 2 as well as methods for augmenting or enhancing or modifying the organoleptic properties, e.g., taste and aroma of said foodstuffs. The methyl(methylthioalkyl)-1,3-dithiolanes of U.S. Pat. No. 4,472,446 are indicated therein to augment or enhance meat, turkey, hydrolyzed vegetable protein, mushroom, bread-like, meat extract, beef broth, pot roast, onion and brothy flavored foodstuffs.

The methyl(methylthioalkyl)-1-3-dithiolanes of U.S. Pat. No. 4,472,446 are indicated therein to provide meaty, hydrolyzed vegetable protein-like, sweet, meat extract-like, mushroom-like, turkey-like, chicken-like, pork-like and butterscotch-like aroma nuances and oniony, onion/roasted hydrolyzed vegetable protein-like, sweet, meaty, meat extract-like, bready, mushroom-like, turkey-like, chicken-like, pork-like and butterscotch-like taste nuances.

Nothing in the prior art discloses the dialkylthioalkenes, dialkylthioalkylcycloalkenes and monoalkylthioalkeneylcycloalkenes of our invention or uses thereof in augmenting or enhancing the aroma or taste of foodstuffs, chewing gums, toothpastes and medicinal products. The dialkylthioalkenes, dialkylthioalkylcycloalkenes and monoalkylthioalkeneylcycloalkenes of our invention and organoleptic uses thereof are unobvious, unexpected and advantageous with respect to other acetals or ketals of the prior art.

BRIEF DESCRIPTION OF THE DRAWINGS

FIG. 1 is the NMR spectrum for the compound having the structure:

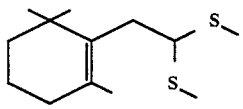

prepared according to Example I (Conditions: Field strength: 100 MHz; Solvent: $CFCl_3$).

FIG. 2 is the NMR spectrum for the mixture produced according to Example II(A) of compounds having the structures:

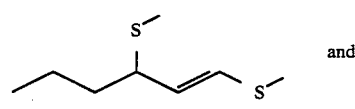

and

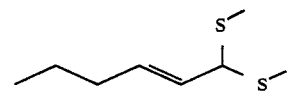

with the mole ratio of the compound having the structures:

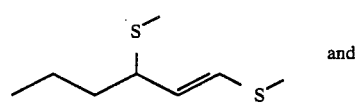

and

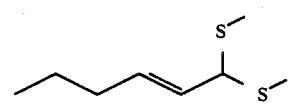

being approximately 8:2 (Conditions: Field strength: 100 MHz; Solvent: CFCl₃).

FIG. 3 is the NMR spectrum of the mixture of compounds having the structures:

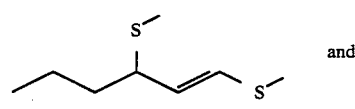

and

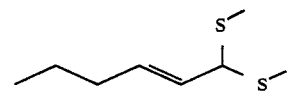

prepared according to Example II(B) with the mole ratio of the compound having the structure:

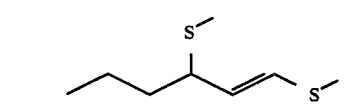

to the compound having the structure:

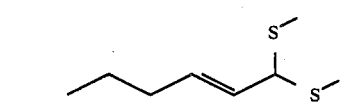

being approximately 65:30 (Conditions: Field strength: 100 MHz; Solvent: CFCl₃).

FIG. 4 is the NMR spectrum for the mixture of compounds having the structures:

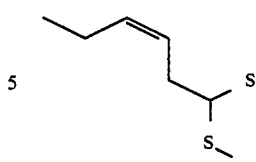 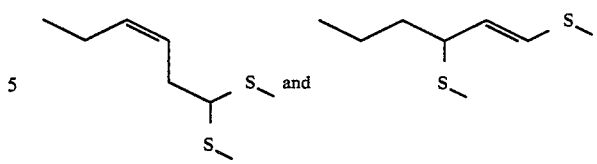

prepared according to Example III. The mole ratio of the compound having the structure:

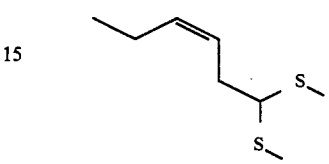

to the compound having the structure:

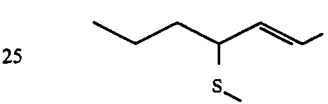

is approximately 65:35. (Conditions: Field strength: 100 MHz; Solvent: CFCl₃).

FIG. 5 is the NMR spectrum for the mixture of compounds having the structures:

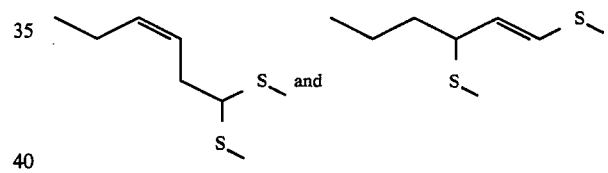

produced according to Example III. (Conditions: Field strength: 100 MHz; Solvent: CFCl₃).

FIG. 6 is the NMR spectrum for the compound having the structure:

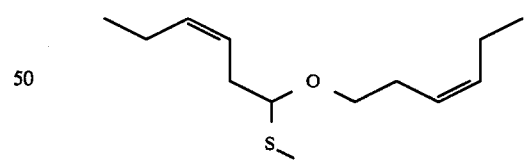

produced according to Example III. (Conditions: Field strength: 100 MHz; Solvent: CFCl₃).

FIG. 7 is the NMR spectrum for the compound having the structure:

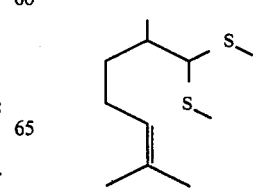

prepared according to Example IV (Conditions: Field strength: 100 MHz; Solvent: CFCl₃).

Figure 8:
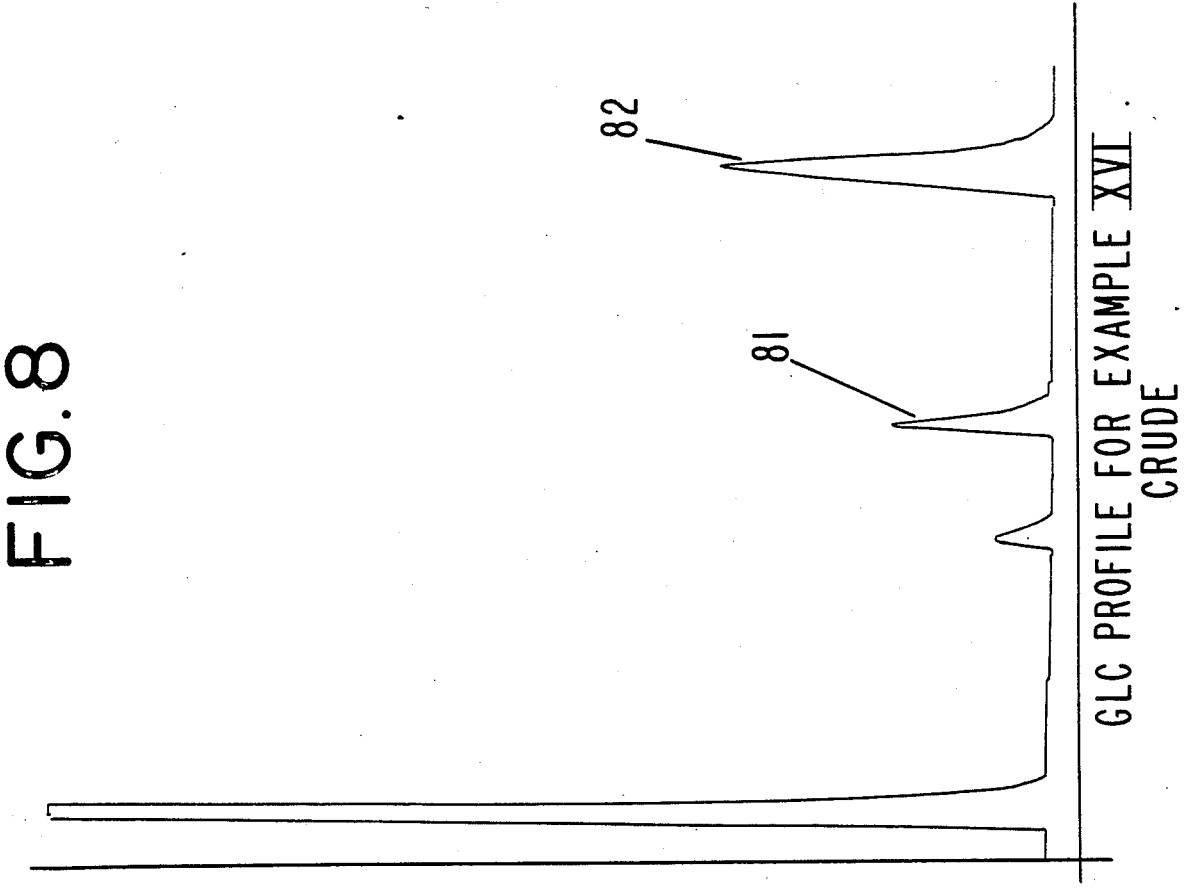

FIG. 8 is the GLC profile for the crude reaction product of Example XVI containing the compounds having the structures:

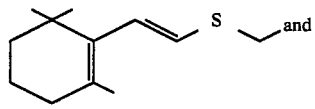and

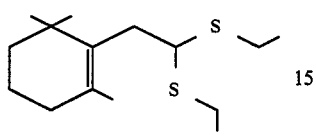

(Conditions: Carbowax column programmed at 100°-220° C. at 8° C. per minute.

Figure 9:
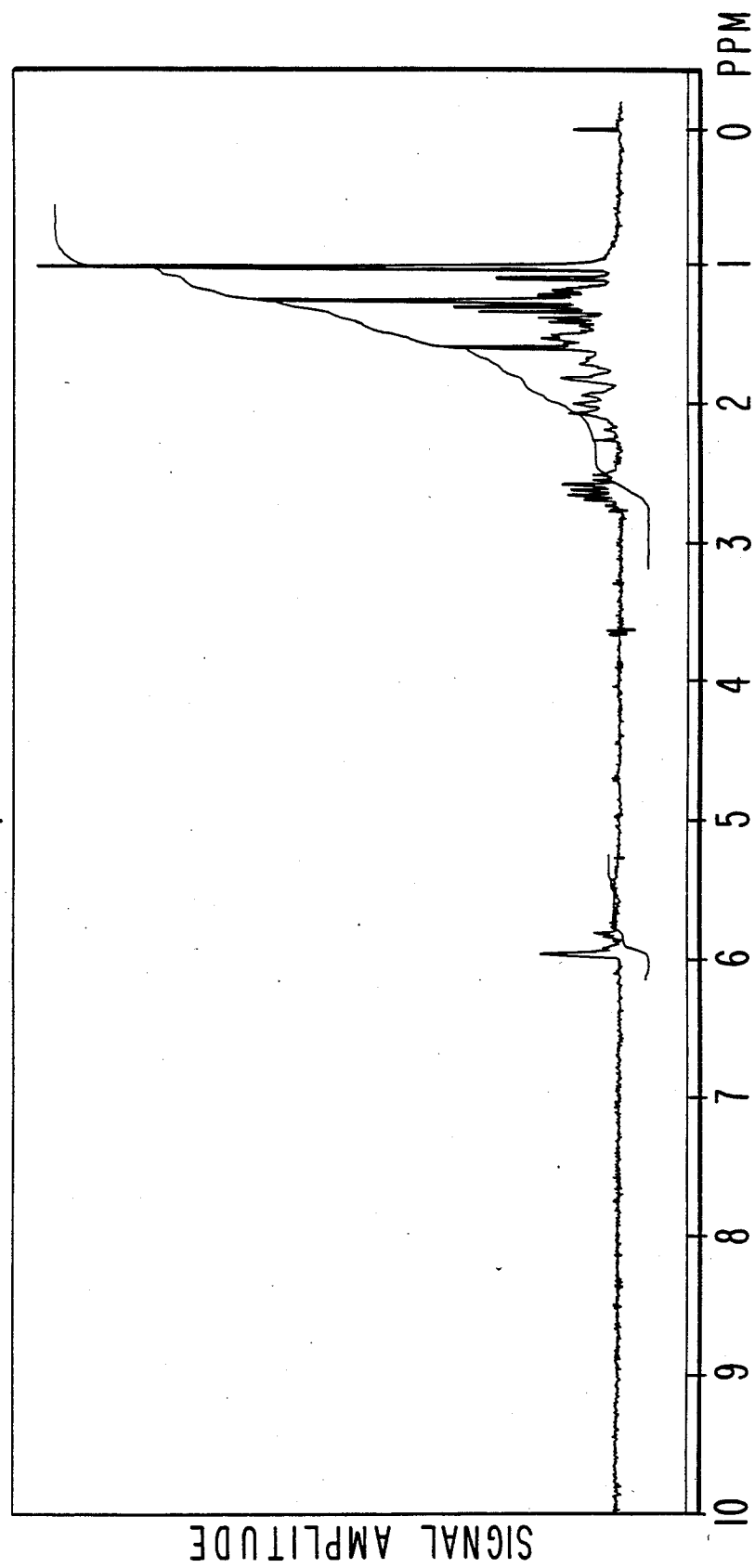

FIG. 9 is the NMR spectrum for the compound having the structure:

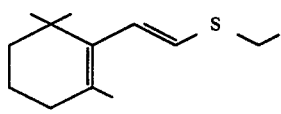

of the peak indicated by reference numeral 81 of the GLC profile of FIG. 8, produced according to Example XVI (Conditions: Field strength: 100 MHz; Solvent: CFCl₃).

Figure 10:
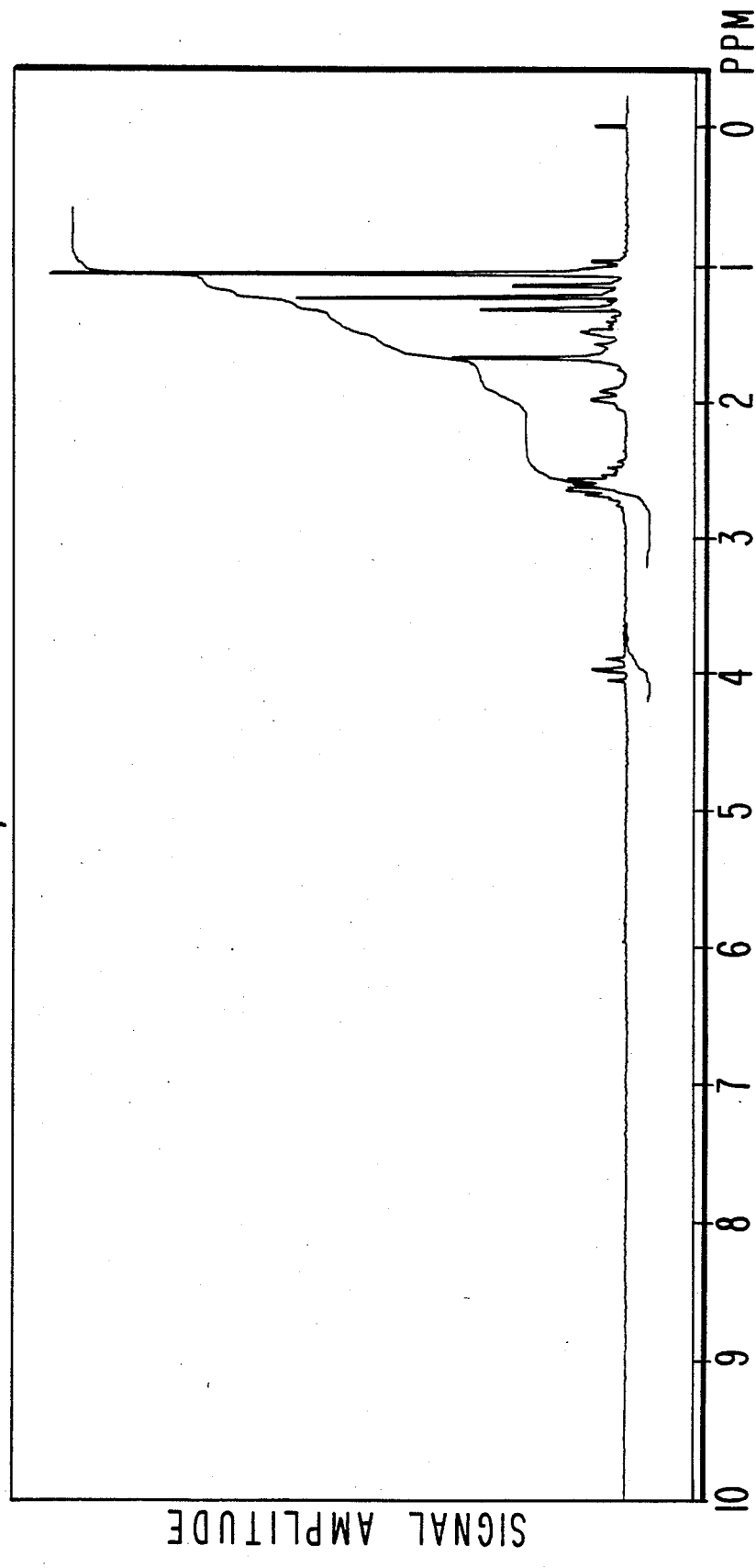

FIG. 10 is the NMR spectrum for the compound having the structure:

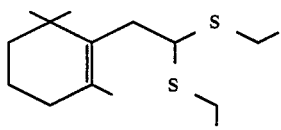

of the peak indicated by reference numeral 82 of FIG. 8, produced according to Example XVI (Conditions: Field strength: 100 MHz; Solvent: CFCl₃).

Figure 11:
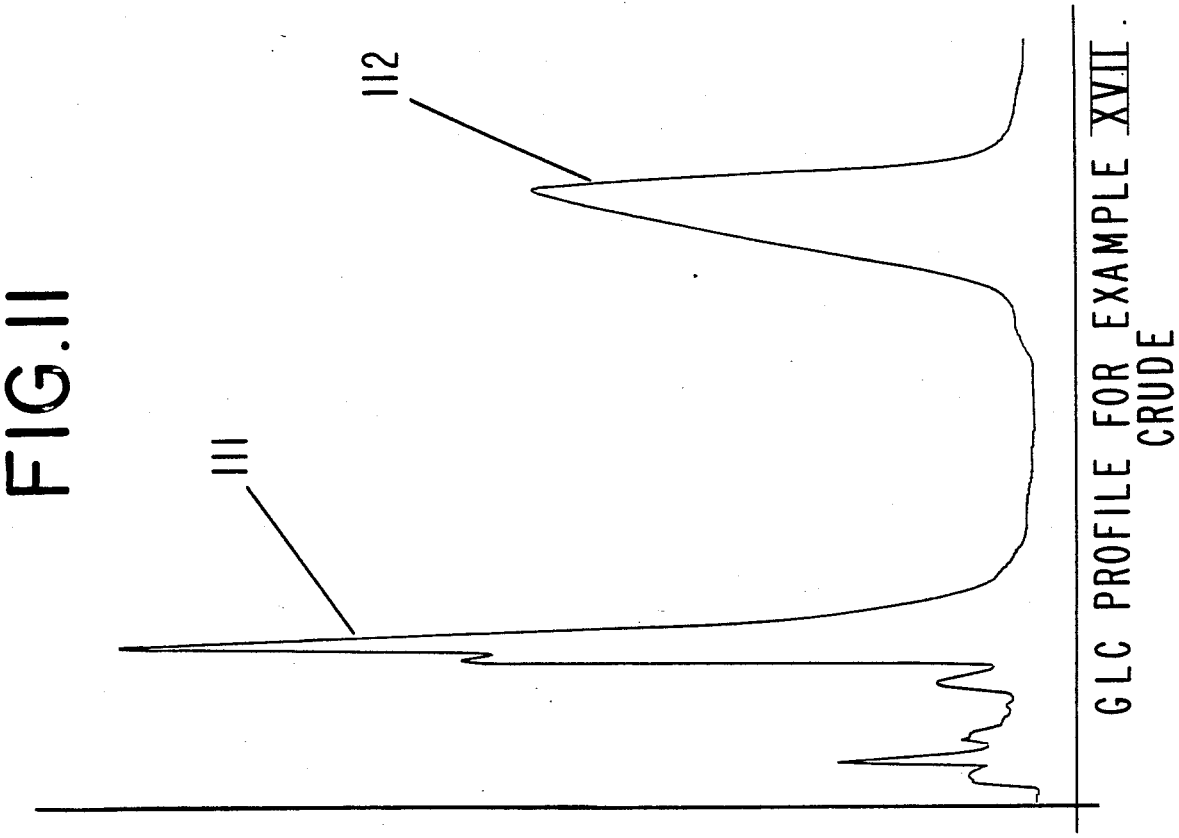

FIG. 11 is the GLC profile for the crude reaction product produced according to Example XVII containing the compounds having the structures:

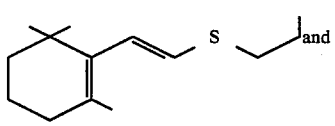and

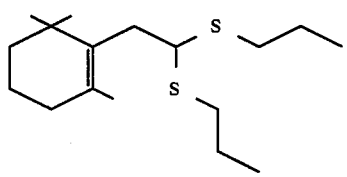

(Conditions: Carbowax column programmed at 220° C. isothermal).

FIG. 12 is the NMR spectrum for the peak indicated by reference numeral 111 of FIG. 11, for the compound having the structure:

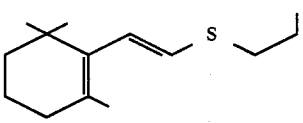

(Conditions: Field strength: 100 MHz; Solvent: CFCl₃).100.

FIG. 13 is the NMR spectrum for the compound having the structure:

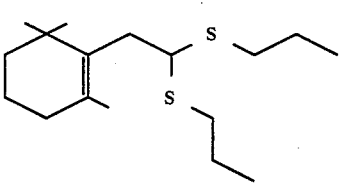

produced according to Example XVII, of the peak indicated by reference numeral 112 of FIG. 11. (Conditions: Field strength: 100 MHz; Solvent: CFCl₃).

Figure 14:
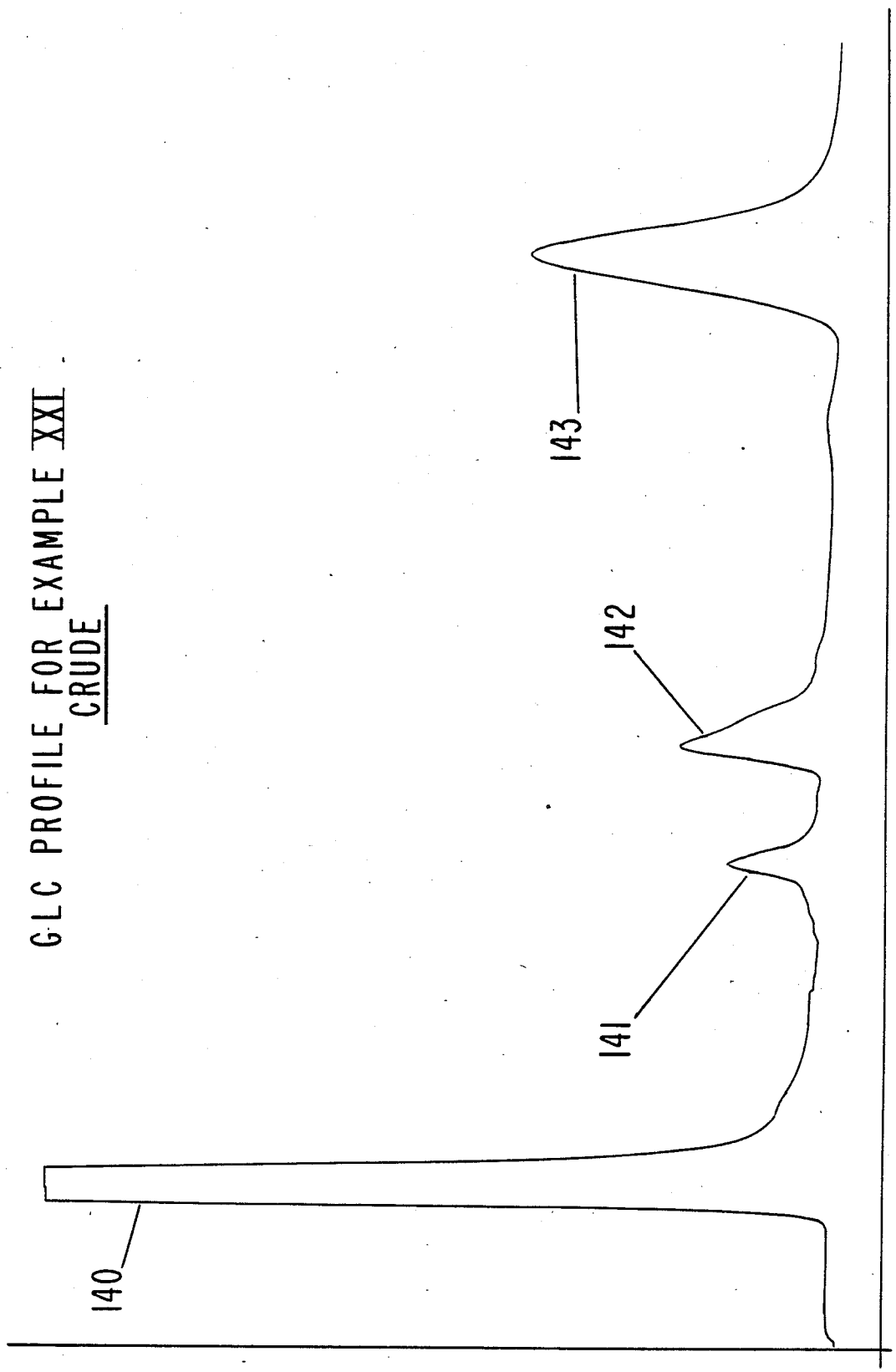

FIG. 14 is the GLC profile for the crude reaction product of Example XXI containing the compounds having the structures:

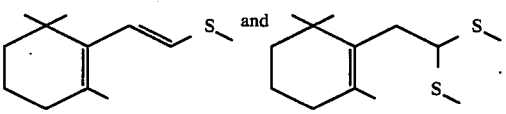

FIG. 15 is the GLC profile for Fraction 5 of the distillation of the reaction product of Example XXI containing 80% by weight of the compound having the structure:

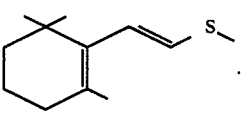

FIG. 16 is the NMR spectrum for Fraction 5 of the distillation of the reaction product of Example XXI containing the compound having the structure:

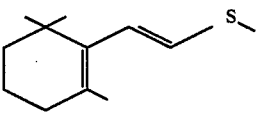

(Conditions: Field strength: 100 MHz; Solvent: CFCl₃).

FIG. 17 is the NMR spectrum for purified Fraction 5 of the distillation of the reaction product of Example XXI containing 85% by weight of the compound having the structure:

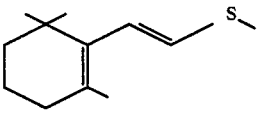

("Z":"E" ratio=2:1).

DETAILED DESCRIPTION OF THE DRAWINGS

FIG. 8 is the GLC profile for the crude reaction product of Example XVII containing the compounds having the structures:

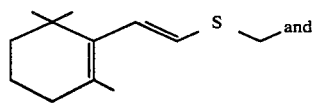

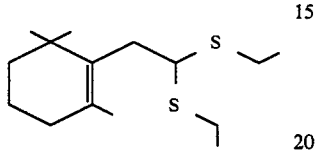

(Conditions: Carbowax column programmed at 100°–220° C. at 8° C. per minute).

The peak indicated by reference numeral 81 is the peak for the compound having the structure:

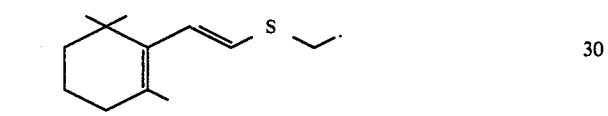

The peak indicated by reference numeral 82 is the peak for the compound having the structure:

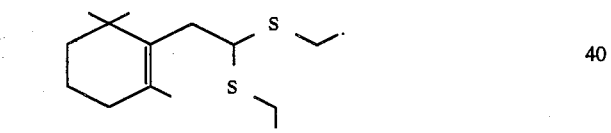

FIG. 11 is the GLC profile for the crude reaction product of Example XVII containing the compounds having the structures:

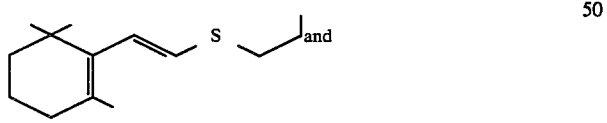

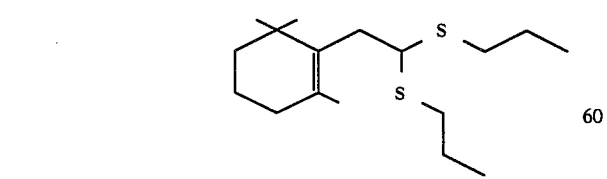

(Conditions: Carbowax column programmed at 220° C. isothermal).

The peak indicated by reference numeral 111 is the peak for the compound having the structure:

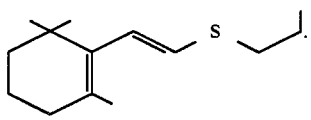

The peak indicated by reference numeral 112 is the peak for the compound having the structure:

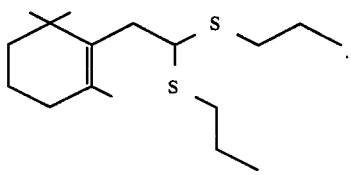

FIG. 14 is the GLC profile for the crude reaction product of Example XXI containing the compounds having the structures:

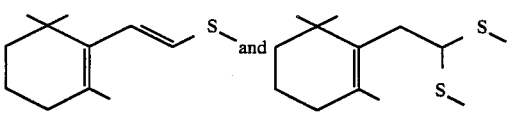

(Conditions: SE-30 column programmed at 100°–220° C. at 8° C. per minute). The peak indicated by reference numeral 140 is the peak for the reaction solvent, methylene chloride. The peak indicated by reference numeral 141 is the peak for the starting material, β-homocyclocitral having the structure:

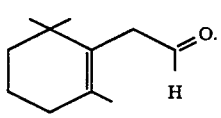

The peak indicated by reference numeral 142 is the peak for the compound having the structure:

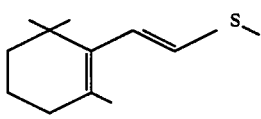

The peak indicated by reference numeral 143 is the peak for the compound having the structure:

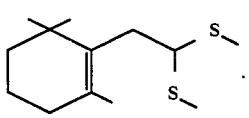

FIG. 15 is the GLC profile for Fraction 5 of the distillation of the reaction product of Example XXI containing the compound having the structure:

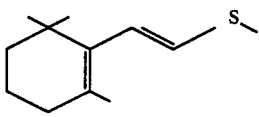

(Conditions: 8'×0.125" SE-30 column programmed at 100°-220° C. at 8° C. per minute). The peak indicated by reference numeral 150 is the peak for the compound having the structure:

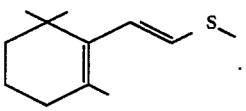

INVENTION

The present invention provides the novel dialkylthioalkenes, dialkylthioalkylcycloalkenes and monoalkylthioalkeneylcycloalkenes useful for augmenting or enhancing the aroma or taste of foodstuffs, chewing gums, toothpastes and medicinal products, said dialkylthioalkenes, dialkylthioalkylcycloalkenes and monoalkylthioalkeneylcycloalkenes being defined according to the generic structure:

wherein R represents $C_6$-$C_{11}$ alkenyl or cycloalkenylalkyl and $R_2$ represents $C_1$-$C_3$ alkyl as well as methods for augmenting or enhancing or modifying the organoleptic properties, e.g., taste and aroma of said foodstuffs, chewing gums, medicinal products and toothpastes. The genus defined according to the structure:

also includes the subgenus having the structure:

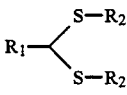

wherein $R_2$ represents $C_1$-$C_3$ alkyl and $R_1$ represents $C_5$-$C_{10}$ alkenyl or cycloalkenylalkyl.

The dialkylthioalkenes, dialkylthioalkylcycloalkenes and monoalkylthioalkeneylcycloalkenes of our invention augment or enhance blueberry, raspberry, blackcurrant, guava, tropical fruit, garlic, hydrolyzed vegetable protein and cooked bean flavored foodstuffs, chewing gums, toothpastes, and medicinal products. The dialkylthioalkenes, dialkylthioalkylcycloalkenes and monoalkylthioalkeneylcycloalkenes of our invention provide blueberry, blackcurrant, vanilla, guava, grapefruit, galbanum-like, tomato, sulfury, garlic, green, hydrolyzed vegetable protein-like, beany and cooked vegetable fried onion, floral, roasted, onion, crisp roasted, bacon, sweet, cherry and marachino cherry-like aroma and taste nuances.

The dialkylthioalkenes, dialkylthioalkylcycloalkenes and monoalkylthioalkeneylcycloalkenes of our invention defined according to the generic structure:

wherein R represents $C_6$-$C_{11}$ alkenyl or cycloalkenyl alkyl and $R_2$ represents $C_1$-$C_3$ alkyl may be produced by means of reacting an alkyl mercaptan having the structure:

$$R_2\text{—SH}$$

with an aldehyde having the structure:

wherein $R_1$ represents $C_5$-$C_{10}$ alkenyl or cycloalkenylalkyl and $R_2$ represents $C_1$-$C_3$ alkyl in the presence of a protonic acid catalyst such as paratoluene sulfonic acid, xythene sulfonic acid, methan sulfonic acid, phosphoric acid and concentrated sulfuric acid.

The reaction may be illustrated thusly:

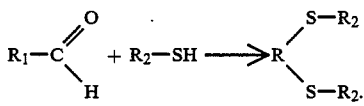

The reaction temperature may vary from about 0° C. up to about 25° C. with a preferred reaction temperature range of 0°–10° C. The reaction time may vary from about 5 hours up to about 20 hours. The reaction takes place by bubbling in the alkyl mercaptan having the structure:

$$R_2\text{—SH}$$

into the reaction mass which contains in addition to reactant aldehyde having the structure:

a suitable solvent. The solvent for the reaction is one that is inert to both the products and the reactants and is also one that may easily be recovered from the reaction mass as by complete removal on distillation, in view of the fact that the reaction mass as by complete removal on distillation, in view of the fact that the reaction products are used as food flavors, medicinal product flavors, chewing gum flavors and toothpaste flavors for internal consumption. Accordingly, suitable solvents are cyclohexane, cyclopentane, cyclooctane, 1-methylcyclohexane, 1,2-dimethylcyclohexane, 1,2,4-trimethylcyclohexane, methylene chloride ($CH_2$-$Cl_2$), 2-ethyltetrahydrofuran, 2,5-dimethyltetrahydrofuran and the like.

Examples of the products of our invention and their organoleptic properties are as follows:

TABLE I

| Structure of compound or compounds (if in admixture): | Organoleptic Properties |
|---|---|
| 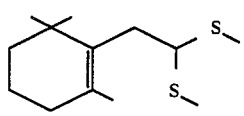<br>prepared according to Example I. | A blueberry, blackcurrant and vanilla aroma and taste profile at 3 ppm causing it to be useful in blueberry, raspberry and blackcurrant flavored foodstuffs. |
| Mixture of compounds having the structures:<br>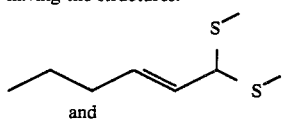<br>and<br>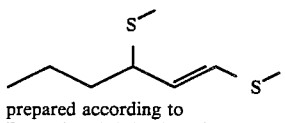<br>prepared according to Example II(A) (mole ratio of compound having the structure:<br>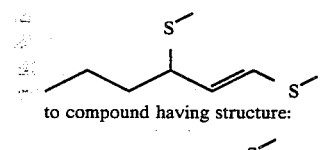<br>to compound having structure:<br>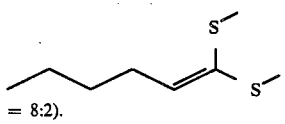<br>= 8:2). | A guava, grapefruit, galbanum, tomato and sulfury aroma and taste profile at 0.2 ppm causing it to be useful in guava and tropical fruit flavored foodstuffs. |
| Mixture of compounds having the structures:<br>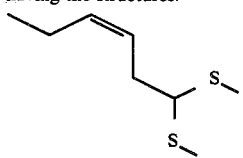<br>and<br>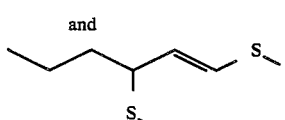<br>prepared according to Example III (ratio of compound having the structure:<br>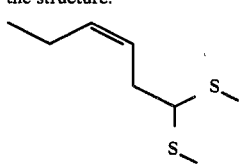<br>and<br>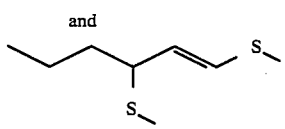<br>= 65:35). | A garlic and green aroma and taste profile at 1 ppm causing it to be useful in garlic and onion flavored foodstuffs. |

TABLE I-continued

| Structure of compound or compounds (if in admixture): | Organoleptic Properties |
|---|---|
| Compound having the structure:<br>[structure]<br>prepared according to Example IV. | A hydrolyzed vegetable protein-like, beany, cooked vegetable aroma and taste profile at 0.01 ppm causing it to be useful in hydrolyzed vegetable protein, meaty and cooked bean flavored foodstuffs. |
| Compound having the structure:<br>[structure]<br>prepared according to Example XVI. | A garlic and fried onion aroma and taste profile at 20 ppm causing it to be useful in onion soups and garlic flavored foodstuffs. |
| Compound having the structure:<br>[structure]<br>produced according to Example XVI. | A floral, green and roasted aroma and taste profile at 0.5 ppm causing it to be useful in almond, roasted peanut and baked goods flavored foodstuffs. |
| Compound having the structure:<br>[structure]<br>produced according to Example XVII. | An oniony, roasted, crisp roasted bacon aroma and taste profile at 2 ppm causing it to be useful in bacon, roasted nut, roasted onion, almond and peanut flavored foodstuffs. |
| Compound having the structure:<br>[structure]<br>prepared according to Example XVII. | A sweet, cherry, marachino, cherry, oniony and bacon aroma and taste profile at 0.1 ppm causing it to be useful in cherry and black cherry flavored foodstuffs. |

At the end of the reaction as stated, supra, the reaction product is extracted from the reaction mass or the reaction mass is washed, for example, with saturated sodium chloride. The reaction product is then distilled preferably by means of vacuum distillation.

Thus, dialkylthioalkenes, dialkylthioalkylcycloalkenes and monoalkylthioalkenylcycloalkenes produced according to our invention can be used to alter, vary, fortify, modify, enhance or otherwise improve the organoleptic properties, including flavor and/or aroma, of a wide variety of materials which are ingested, consumed, or otherwise organoleptically sensed.

The term "alter" in its various forms will be understood herein to mean the supplying or imparting a flavor character or note to an otherwise bland, relatively tasteless substance, or augmenting an existing flavor characteristic where the natural flavor is deficient in some regard, or supplementing the existing flavor or aroma impression to modify the organoleptic character. The materials which are so altered are generally referred to herein as consumable materials.

Such dialkylthioalkenes, dialkylthioalkylcycloalkenes and monoalkylthioalkenylcycloalkenes of our invention are accordingly useful in flavoring compositions. Flavoring compositions are hereintaken to mean those which contribute a part of the overall flavor impression by supplementing or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs includes meats, gravies, soups, convenience foods, malt and other alcoholic or non-alcoholic beverages, milk and dairy products, nut butters such as peanut butter and other spreads, seafoods including fish, crustaceans, mollusks and the like, candies, breakfast foods, baked goods, vegetables, cereals, soft drinks, snack foods, dog and cat foods, other veterinary products, and the like.

When the dialkylthioalkenes, dialkylthioalkylcycloalkenes and monoalkylthioalkenylcycloalkenes according to this invention are used in a food flavoring composition, they can be combined with conventional flavoring materials or adjuvants. Such co-ingredients or flavoring adjuvants are well known in the art for such use and have been extensively described in the literature. Apart from the requirement that any such adjuvant material is ingestibly acceptable, and thus non-toxic or otherwise non-deleterious, conventional materials can be used and broadly include other flavor materials, vehicles, stabilizers, thickeners, surface active agents, conditioners and flavor intensifiers.

Examples of preferred co-flavoring adjuvants are:
Methyl thiazole alcohol (4-methyl-5-beta-hydroxyethyl thiazole);
2-Methyl butanethiol;
4-Mercapto-2-butanone;
3-Mercapto-2-pentanone;
1-Mercapto-2-propanone;
Benzaldehyde;
Furfural;
Furfuryl alcohol;
2-Mercapto propionic acid;
Alkyl pyrazine;
Methyl pyrazine;
2-Ethyl-3-methyl pyrazine;
Tetramethyl pyrazine;
Polysulfides;
Dipropyl disulfide;
Methyl benzyl disulfide;
Alkyl thiophenes;
2-Butyl thiophene;
2,3-Dimethyl thiophene;
5-Methyl furfural;
Acetyl furan;
2,4-Decadienal;
Guiacol;
Phenyl acetaldehyde;
β-Decalactone;
d-Limonene;
Acetoin;
Amyl acetate;
Maltol;
Ethyl butyrate;
Luvulinic acid;
Piperonal;
Ethyl acetate;
n-Octanal;
n-Pentanal;
n-Hexanal;
Diacetyl;
Monosodium glutamate;
Monopotassium glutamate;
Sulfur-containing amino acids, e.g., Cysteine;
Hydrolyzed vegetable protein;
2-Methylfuran-3-thiol;
2-Methyldihydrofuran-3-thiol;
2,5-dimethylfuran-3-thiol;
Hydrolyzed fish protein;
Tetramethyl pyrazine;
Propylpropenyl disulfide;
Propylpropenyl trisulfide;
Diallyl disulfide;
Diallyl trisulfide;
Dipropenyl disulfide;
Dipropenyl trisulfide;
4-Methyl-2-[methylthio)-ethyl]-1,3-dithiolane;
4,5-Dimethyl-2[methylthio)ethyl]-1,3-dithiolane;
4,5-Dimethyl-2-(methylthiomethyl)-1,3-dithiolane;
4-Methyl-2-(methylthiomethyl)-1,3-dithiolane.

The dialkylthioalkenes, dialkylthioalkylcycloalkenes and monoalkylthioalkenylcycloalkenes or the compositions incorporating them, as mentioned above, can be combined with one or more vehicles or carriers for adding them to the particular product. Vehicles can be edible or otherwise suitable materials such as ethyl alcohol, propylene glycol, water and the like. Carriers include materials such as gum arabic, carrageenan, other gums and the like.

The dialkylthioalkenes, dialkylthioalkylcycloalkenes and monoalkylthioalkenylcycloalkenes according to this invention can be incorporated with the carriers by conventional meams such as spray-drying, drum-drying and the like. Such carriers can also include materials for coacervating the dialkylthioalkenes, dialkylthioalkylcycloalkenes and monoalkylthioalkenylcycloalkenes (and other flavoring ingredients, as present) to provide encapsulated products. When the carrier is an emulsion the flavoring composition can also contain emulsifiers such as mono- and diglycerides or fatty acids and the like. With these carriers or vehicles, the desired physical form of the composition can be prepared.

The quantity of dialkylthioalkenes, dialkylthioalkylcycloalkenes and monoalkylthioalkenylcycloalkenes utilized should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff; the amount and type of flavor Initially present in the foodstuff; the further process or treatment steps to which the foodstuff will be subjected; regional and other preference factors; the type of storage; if any, to which the product will be subject; and the preconsumption treatment, such as baking, frying, and so on, given to the product by the ultimate consumer. Accordingly, the terminology "effect amount" and "sufficient amount" is understood in the context of the present invention to be quantitatively adequate to alter the flavor of the foodstuff.

It is accordingly preferred that the ultimate composition containing from about 0.001 parts per million (ppm) to about 250 ppm of dialkylthioalkenes, dialkylthioalkylcycloalkenes and monoalkylthioalkenylcycloalkenes or mixtures thereof. More particularly, in food compositions it is desirable to use from about 0.001 ppm to 100 ppm for enhancing flavors and in certain preferred embodiments of the invention, from about 0.001 to 50 ppm of the derivatives are included to add positive flavors to the finished product.

The dialkylthioalkenes, dialkylthioalkylcycloalkenes and monoalkylthioalkenylcycloalkenes or mixtures thereof of our invention to be utilized in flavoring compositions can be varied over a wide range depending upon the particular quality to be added to the foodstuff. Thus, amounts of one or more derivatives according to the present invention of from about 0.05 ppm up to 80 or 90 percent of the total flavoring composition can be incorporated in such compositions. It is generally found to be desirable to include from about 0.05 ppm up to about 0.1 percent of the dialkylthioalkenes, dialkylthioalkylcycloalkenes and monoalkylthioalkenylcycloalkenes in such compositions.

The following examples are given to illustrate embodiment of the invention as it is preferred to practice it. It will be understood that these examples are illustrative and the invention is not to be considered as restrictive thereto except as indicated in the appended claims.

All parts, proportions, percentages, and ratios here are by weight unless otherwise indicated.

EXAMPLE I

Preparation of 2-[2,2-bis(methylthio)ethyl]-1,3-trimethylcyclohexene

Reaction:

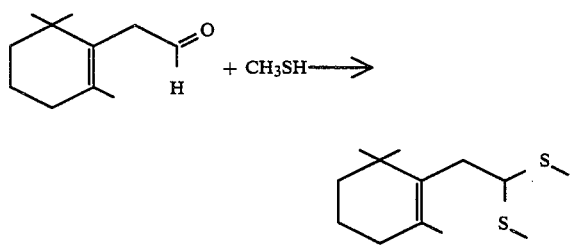

Into a 500 cc reaction flask equipped with stirrer, thermometer, reflux condenser, heating mantle and gas bubbler are placed 200 ml cyclohexane; 0.5 grams paratoluene sulfonic acid and 25 grams of homocyclocitral having the structure:

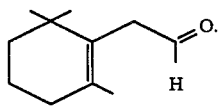

The resulting mixture is then stirred and cooled using an isopropylalcohol ice bath down to 0° C. Over a period of 8 hours with stirring while maintaining the reaction temperature at 0° C., 25 grams of methyl mercaptan is bubbled into the reaction mass. At the end of the addition of the methyl mercaptan, the reaction mass is stirred for a period of 8 hours at 0° C. At the end of this period, the reaction mass is washed with 3 volumes of saturated sodium chloride solution followed by 10 percent sodium bicarbonate solution. 10 percent sodium bicarbonate solution. The reaction mass is then fractionally distilled yielding the product having the structure:

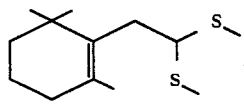

This product has an excellent blueberry, blackcurrant and vanilla aroma and taste profile at 3 ppm causing it to be useful in blueberry, raspberry and blackcurrant flavored foodstuffs, e.g., blackberry flavored beverages, raspberry flavored gelatin deserts and blackcurrant preserves (e.g., blackcurrant "jam".

FIG. 1 is the GLC profile of the compound having the structure:

(Conditions: Field strength: 100 MHz; Solvent: CFCl₃).

EXAMPLE II(A)

Preparation of Mixture of 1,1-bis(methylthio)-E-2-hexene and 1,3-bis(methylthio)-E-1-hexene Reaction:

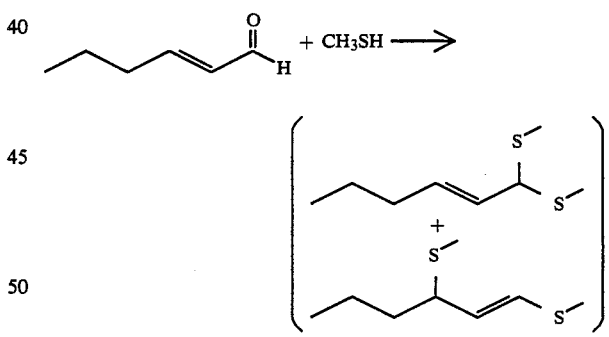

Into a 500 cc reaction flask equipped with stirrer, thermometer, isopropylalcohol cooling bath, reflux condenser and gas bubbler are placed 200 ml cyclohexane; 25 grams of E-2-hexenal and 0.5 grams of paratoluene sulfonic acid. Using the isopropylalcohol/ice cooling bath the reaction mass is cooled to 0° C. Over a period of 12 hours, 50 grams of methyl mercaptan is bubbled into the reaction mass with stirring. The reaction mass is then maintained at 0° C. for a period of 8 hours with stirring. The reaction mass is then washed with 3 volumes of saturated aqueous chloride solution followed by 3 volumes of 10 percent sodium bicarbonate. The reaction mass is then fractionally distilled yielding a mixture of compounds having the structures:

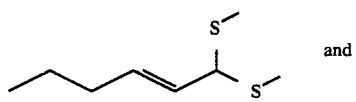 and

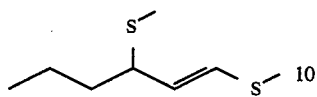

with the mole ratio of the compound having the structure:

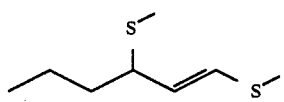

to the compound having the structure:

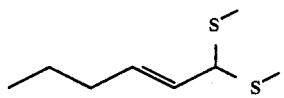

being 8:2. The resulting product has an excellent guava, grapefruit, galbanum, tomato and sulfury aroma and taste profile at 0.2 ppm.

FIG. 2 is the NMR spectrum for the resulting mixture of compounds having the structure:

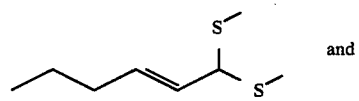 and

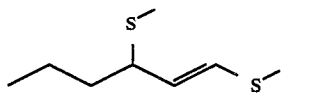

(Conditions: Field strength: 100 MHz; Solvent: CFCl₃).

EXAMPLE II(B)

Another reaction is run using the above conditions except that 200 ml methylene chloride is used instead of 200 ml cyclohexane. In addition, the reaction is run at 10° C. instead of 0° C.

The resulting product is a mixture of compounds having the structures:

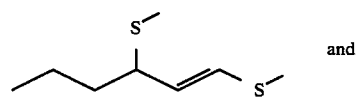 and

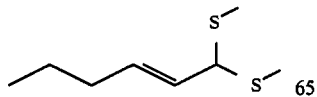

with the mole ratio of the compound having the structure:

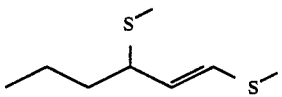

to the compound having the structure:

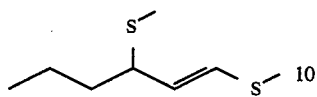

being 65:30.

FIG. 3 is the NMR spectrum for the resulting mixture. (Conditions: Field strength: 100 MHz; Solvent: CFCl₃).

The resulting mixture has an excellent guava, grapefruit, galbanum, tomato and sulfury aroma and taste profile at 0.2 ppm causing it to be useful in guava and tropical fruit flavored foodstuffs, for example, guava nectar and tropical fruit flavored juices.

EXAMPLE III

Preparation of Mixture of
1,1-bis(methylthio)-Z-3-hexene;
1,3-bis(methylthio)-E-1-hexene and
1-[(3-hexenyl)oxy]-1-(methylthio)-Z-Z-3-hexene Reaction:

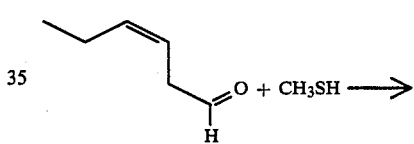

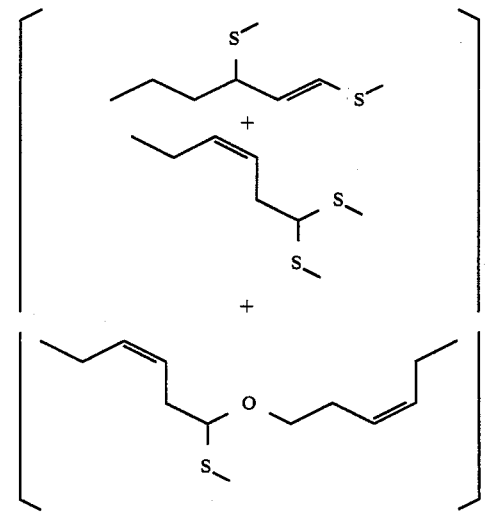

Into a 500 cc reaction flask equipped with stirrer, thermometer, reflux condenser and gas bubbler is placed 200 ml methylene dichloride (CH₂Cl₂; 0.5 grams of paratoluene sulphonic acid and 27 grams of cis-3-hexenal. The reaction mass is cooled to 0° C. with an isopropional ice bath. With stirring over a period of 8 hours, 10 grams of methyl mercaptan is bubbled into the reaction mass. At the end of the 8 hour period, the reaction mass is washed with 3 volumes of saturated aqueous sodium chloride followed by 3 volumes of 10 percent aqueous sodium bicarbonate solution. The reaction mass is then dried over anhydrous sodium sulfate, stripped of solvent and fractionally distilled yielding a mixture of the compounds having the structures:

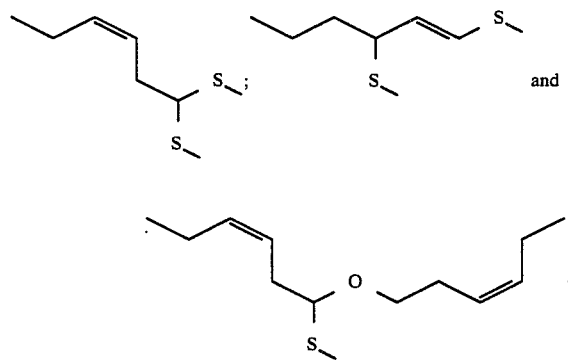

The compound having the structure:

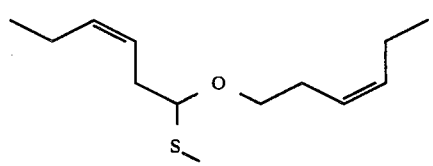

is separated from the mixture of compounds having the structures:

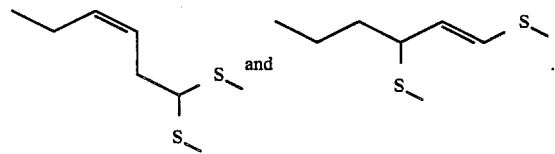

The mixture of compounds having the structures:

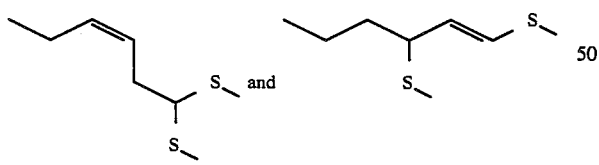

is a mole ratio of 65:35 of the compound having the structure:

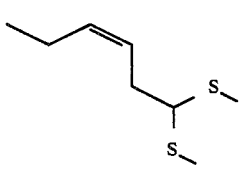

to the compound having the structure:

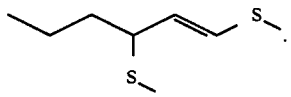

A resulting 65:35 mixture of compounds having the structures:

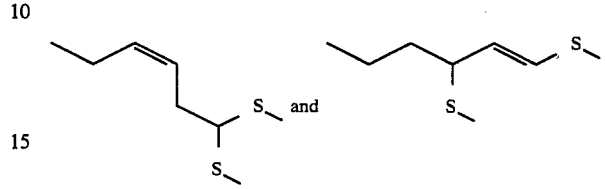

as an intense, fresh garlic, green aroma profile with a garlic, green and sulfury taste at 1 ppm causing it to be useful in garlic and onion flavored foodstuffs.

FIG. 4 is the NMR spectrum for the mixture of compounds having the structures:

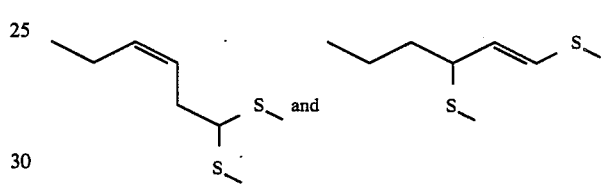

with the mole ratio of the compound having the structure:

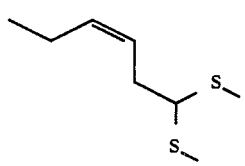

to the compound having the structure:

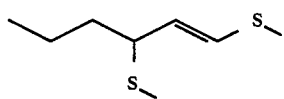

being 65:35. (Conditions: Field strength: 100 MHz; Solvent: CFCl₃).

FIG. 5 is the NMR spectrum of the mixture of compounds having the structures:

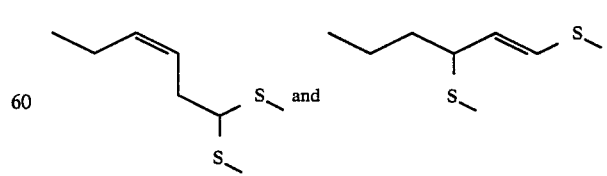

subsequent to re-purification (Conditions: Field strength: 100 MHz; Solvent: CFCl₃).

FIG. 6 is the NMR spectrum for the compound having the structure:

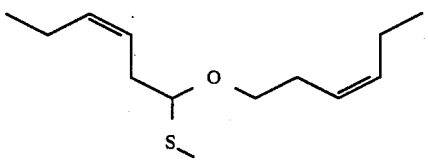

(Conditions: Field strength: 100 MHz; Solvent: CFCl₃).

EXAMPLE IV

Preparation of 2,6-dimethyl-7,7-bis(methylthio)-2-heptene

Reaction:

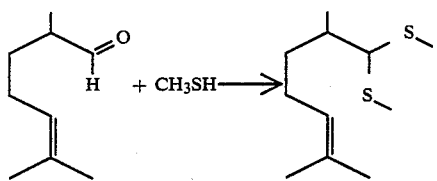

Into a 500 cc reaction flask equipped with stirrer, thermometer, reflux condenser, cooling bath and gas bubbler is placed 200 ml of methylene dichloride (CH₂Cl₂); 0.5 grams paratoluene sulfonic acid and 23.0 grams of melonal having the structure:

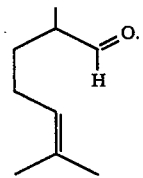

The reaction mass is cooled to 0° C. using the ice-isopropyl alcohol cooling bath. With stirring over a period of 12 hours, 25 grams of methyl mercaptan is bubbled into the reaction flask. The reaction mixture is stirred at 0° C. for another 3 hours. At the end of this period, the reaction mass is washed with 3 volumes of aqueous saturated sodium chloride followed by 3 volumes of 10 percent sodium bicarbonate solution. The solvent is stripped off and the reaction mass is then fractionally distilled yielding the compound having the structure:

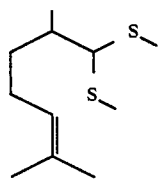

in 99 percent pure form. This compound has an excellent hydrolyzed vegetable protein-like, beany and cooked vegetable aroma and taste profile at 0.01 ppm causing it to be useful in hydrolyzed vegetable protein and cooked bean flavored foodstuffs.

FIG. 7 is the NMR spectrum for the compound having the structure:

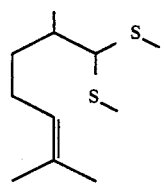

(Conditions: Field strength: 100 MHz; Solvent: CFCl₃).

EXAMPLE V

True Fruit Flavor

The following "true fruit flavor" formulation is prepared:

| Ingredients | Parts by Weight |
| --- | --- |
| Heliotropine | 10.0 |
| Benzaldehyde | 5.0 |
| Paratoluacetaldehyde | 3.2 |
| Vanillin | 2.0 |
| Ethyl-3-methyl-3-phenyl glycidate | 4.0 |
| Phenylethylacetaldelye | 2.1 |
| Benzylacetate | 2.3 |
| Maltol | 2.0 |
| Benzylalcohol | 6.2 |
| Ethyl maltol | 2.4 |
| Cis-2-methyl-2-pentenoic acid | 3.4 |
| 3,4-pentadienoic acid, ethyl ester | 4.1 |
| The compound having the structure: 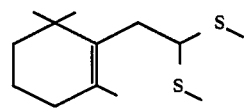 prepared according to Example I, supra. | 2.8 |
| Propylene glyco | 70.0 |

The resulting true fruit flavor is compared in water at the rate of 20 ppm with and without the addition of the compound having the structure:

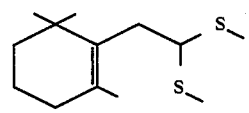

prepared according to Example I. The flavor with the compound having the structure:

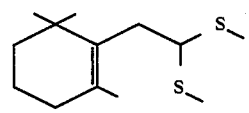

has an excellent, natural, blueberry, blackcurrant character in both aroma and taste. Therefore, it is preferred by a bench panel consisting of five members as being more natural and more characteristic of natural fruit.

EXAMPLE VI

A. Powder Flavor Formulation

20 Grams of the flavor composition of Example V is emulsified in a solution containing 300 gm gum acacia and 700 gm water. The emulsion is spray-dried with a Bown Lab Model Drier utilizing 260 c.f.m. of air with an inlet temperature of 200 F and a wheel speed of 50,000 rpm.

B. Sustained Release Flavor

The following mixture is prepared:

| Ingredients | Parts by Weight |
| --- | --- |
| Liquid True Fruit Flavor Composition of Example V | 20.00 |
| Propylene glycol | 9.00 |
| Cab-O-Sil (Brand of Silica produced by the Cabot Corporation of 125 High Street, Boston, Mass. 02110; Physical Properties: | 5.00 |
| Surface Area: 200 m$^2$/gm Nominal particle size: Density: 2.3 lbs/cu.ft. | 0.012 microns |

Cab-O-Sil is dispersed in the liquid true fruit flavor composition of Example V with vigorous stirring, thereby resulting in a viscous liquid. 71 Parts by weight of the powder flavor composition of Part A, supra, is then blended into the said viscous liquid, with stirring, at 25° C. for a period of 30 minutes resulting in a dry, free flowing sustained release flavor powder.

EXAMPLE VII

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example V is added to the solution which is then homogenized to form an emulsion having particle size typically in the range of 2-5 microns. This material is kept at 120° F. under which conditions the gelatin will not jell.

Coacervation is induced by adding slowly and uniformly 40 parts by weight of a 20 percent aqueous solution of sodium sulphate. During coacervation the gelatin molecules are deposited uniformly about each oil droplet as a nucleus.

Gelatin is effected by pouring the heated coacervate mixture into 1,000 parts by weight of 7 percent aqueous solution of sodium sulphate at 65° F. The resulting jelled coacervate may be filtered and washed with water at temperatures below the melting point of gelatin, to remove the salt.

Hardening of the filtered cake, in this example, is effected by washing with 200 parts by weight of 37 percent solution of formaldehyde in water. The cake is then washed to remove residual formaldehyde.

EXAMPLE VIII

Chewing Gum

100 Parts by weight of chicle are mixed with 4 parts by weight of the flavor prepared in accordance with Example VI(B). Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long-lasting true fruit flavor with excellent blueberry and blackcurrant nuances.

EXAMPLE IX

Chewing Gum

100 Parts by weight of chicle are mixed with 18 parts by weight of the flavor prepared in accordance with Example VII. 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long-lasting "true fruit" flavor with intense blackberry and blackcurrant aroma and taste nuances.

EXAMPLE X

Toothpaste Formulation

The following separate groups of ingredients are prepared:

| Parts by Weight | Ingredients |
| --- | --- |
| Group "A" | |
| 30.200 | Glycerine |
| 5.325 | Distilled water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N—Lauroyl Sarcosinate (foaming agent) |
| Group "D" | |
| 1.200 | Flavor material of Example VI(B) |
| 111.00 | Total |

Procedure:

1. The ingredients in Group "A" are stirred and heated in a stream jacketed kettle to 160° F.
2. Stirring is continued for an additional three to five minutes to form a homogeneous gel.
3. The powders of Group "B" are added to the gel, while mixing, until a homogeneous paste is formed.
4. With stirring, the flavor of "D" is added and lastly the sodium-n-lauroyl sarcosinate.
5. The resultant slurry is then blended for one hour. The completed paste is then transferred to three roller mill and the homogenized, and finally tubed.

The resulting toothpaste when used in a normal toothbrushing procedure yields a pleasant "true fruit" flavor, of constant strong intensity throughout said procedure (1-1.5 minutes).

EXAMPLE XI

Chewable Vitamin Tablets

The flavor material produced according to the process of Example VI(B) is added to a Chewable Vitamin Tablet Formulation at a rate of 10 gm/Kg which Chewable Vitamin Tablet formulation is prepared as follows:

In a Hobart Mixer, the following materials are blended to homogeneity:

|  | Gms/1000 Tablets |
| --- | --- |
| Vitamin C (absorbic acid) as ascorbic acid-sodium ascorbate mixture 1:1 | 70.11 |
| Vitamin B$_1$ (thiamine mononitrate) as Rocoat ® thiamine mononitrate) as Rocoat ® thiamine mononitrate 33⅓% (Hoffman La Roche) | 4.0 |
| Vitamin B$_2$ (riboflavin) as Rocoat ® riboflavin 33⅓% | 5.0 |
| Vitamin B$_6$ (pyridoxine hydrochloride) as Rocoat ® pyridoxine hydrochloride 33⅓% | 4.0 |
| Niacinamide as Rocoat ® niacinamide 33⅓% | 3.0 |
| Calcium pantothenate | 11.5 |
| Vitamin B$_{12}$ (cyanocobalamin) as Merck 0.1% in gelatin | 3.5 |
| Vitamin E (dl-alpha-tocopheryl acetate) as dry Vitamin E acetate 33⅓% | 6.6 |
| d-Biotin | 0.044 |
| Flavor Example IV(B) | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 Grams dry Vitamin A Acetate and 0.6 grams Vitamin D are then added as beadlets. The entire blend is then compressed using concave punches at 0.5 gm each.

Chewing of the resultant tablets yields a pleasant, long-lasting, consistently strong "true fruit" flavor for a period of 12 minutes.

EXAMPLE XII

At the rate of 3 ppm the compound having the structure:

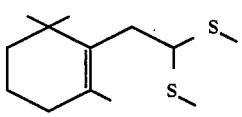

prepared according to Example I placed in a 95% food-grade ethanol solution at the rate of 10% is added to CARMEL KOSHER ® vegetable gel (85 gram package) having the following contents:

Sugar
Carrageenan
Citric acid
Potassium citrate

True fruit flavor of Example V without the compound having the structure:

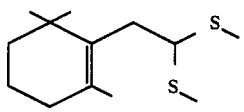

The resulting product is added to 16 ounces of boiling water and stirred for a period of 1.5 minutes. The resulting material is poured into a mold and is permitted to cool. The resulting jell has an excellent "true fruit" flavor with intense blueberry and blackcurrant nuances. Note: CARMEL KOSHER ® vegetable jell is produced by Carmel Kosher Food Products, Inc. of Chicago, Ill. 60632.

EXAMPLE XIII

Guava Nectar

At the rate of 0.2 ppm, the mixture of compounds having the structures:

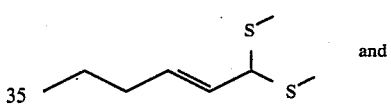

and

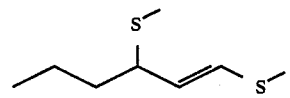

produced according to Example II(A) (ratio of compound having the structure:

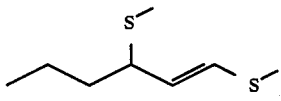

to the compound having the structure:

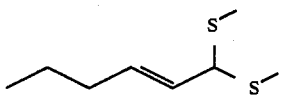

being 80:20) is added to GOYA ® GUAVA NECTAR produced by Goya Products Inc. The resulting guava nectar has a more natural-like taste and the guava nectar not containing the mixture of compounds having the structures:

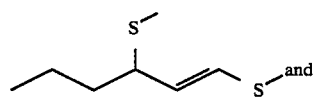

and

-continued

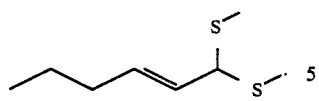

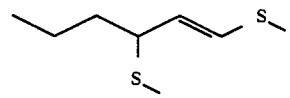

The resulting guava nectar also has a faint, pleasant, aesthetically pleasing grapefruit nuance.

EXAMPLE XIV

Three meat loaf type products are prepared according to the following formulation:

| Ingredients | Amount |
|---|---|
| TVP, minced | 1 cup |
| Ground beef | 1 cup |
| Water | 1 cup |
| Beef suet | ⅛ cup |
| Bread crums, dry, unflavored | 1 cup |
| Whole milk | 1 cup |
| Egg albumen | 3 tbsp. |
| Salt | 1¼ tbsp. |
| Black pepper | ¼ teasp. |
| Catsup | ¼ cup |
| Water | 32 ml. |

1 "TVP" is a texturized vegetable protein mixture made by Archer-Daniels-Midland Company.

Three separate portions prepared according to the foregoing formulation are made into three meat loaves. Loaf A contains no additional additive. Loaf B contains 32 ml of fresh pressed onion juice to replace the 32 ml of water. Loaf C contains 5 ppm of the mixture prepared according to Example III containing the compounds having the structures:

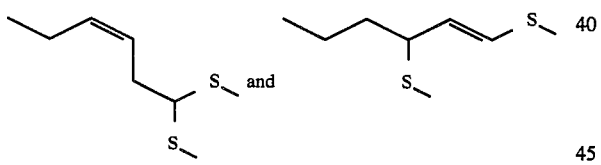

with the ratio of compound having the structure:

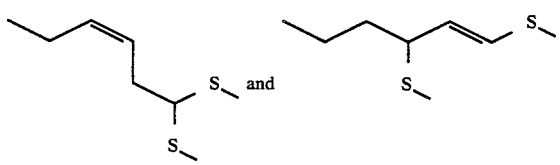

with the ratio of compound having the structure:

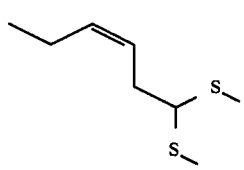

to the compound having the structure:

being 65:30. The three leaves are baked at 350° F. for 1 hour.

The Loaves B and C are judged superior to Loaf A because of the onion character of B and the onion/garlic character of C enhances the overall taste and covers the dry, cardboard-like cereal character of Loaf A.

EXAMPLE XV

The compound having the structure:

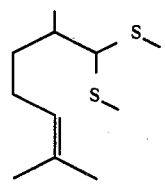

prepared according to Example IV, supra is added to a 2% solution of Wyler's "Beef Flavor Instant Bouillon" (manufactured by Wyler Foods, Division of Borden, Inc., Chicago, Ill., U.S.).

Ingredients salt
hydrolyzed vegetable protein
malto dextrin
sugar beef fat
water
monosodium glutamate
flavorings
corn sugar
beef extract
caramel
color
hydrogenated vegetable fat; and
U.S. certified food color at the rate of 0.1 ppm. The resulting beef flavor has a beany, cooked vegetable, hydrolyzed vegetable protein, sweet and meaty aroma and taste profile. The hydrolyzed vegetable protein nuance are more natural-like and more intense than the beef gravy not containing the compound having the structure:

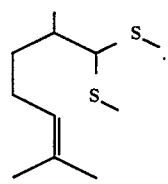

A meat gravy is prepared containing 0.2 ppm by weight of the compound having the structure:

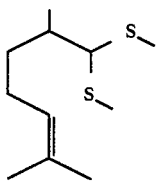

prepared according to Example IV using a beef base and beef fat. The resulting beef gravy containing the compound having the structure:

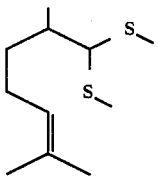

is then added to mushrooms cooked using boiling water at a rate of 10 parts gravy to 100 parts cooked mushroom. The resulting mushroom platter has an excellent natural-like beefy, savoury mushroom flavor with bready and savoury hydrolyzed vegetable protein nuances.

EXAMPLE XVI

Preparation of 2,6,6-trimethyl-1-cyclohexene-1-acid aldehyde Diethyl Mercaptal and 2-[-2-(ethylthio)ethenyl]-1,3,3-trimethyl-cyclohexene Reaction

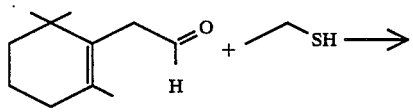

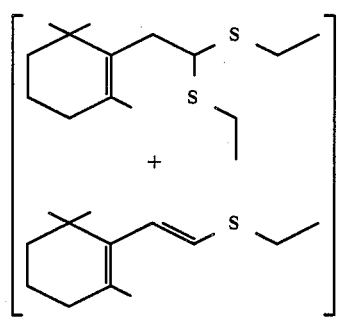

Into a Parr bomb is placed 16.6 grams beta-homocyclocitral having the structure:

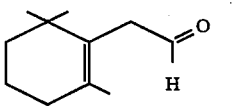

12 grams ethyl mercaptan; 40 ml methyl dichloride and 0.1 grams paratoluene sulfonic acid. The Parr bomb is closed and with stirring, the contents of the Parr bomb is heated to 100° C. The Parr bomb is shaken at 100° C. for a period of 5 hours. At the end of the 5 hour period, the Parr bomb is opened and the contents are washed with two volumes of 10% aqueous sodium carbonate followed by one volume of 50 ml of water. The resulting reaction mass is dried over anhydrous sodium sulfate and the methylene dichloride is evaporated on a Buchi evaporator. The resulting reaction mass is then distilled on a micro distillation column yielding the following fractions:

| Fraction No. | Vapor Temp (0 C.) | Liquid Temp. (0 C.) | Vacuum mm/Hg. Pressure |
|---|---|---|---|
| 1 | 105/94 | /148 | 6 |
| 2 | 97 | 162 | 6 |
| 3 | 130 | 172 | 6 |
| 4 | 143 | 175 | 6 |
| 5 | 160 | 180 | 6 |
| 6 | 160 | 180 | 6 |
| 7 | 155 | 220 | 6 |

The resulting product contains two compounds; the compound having the structure:

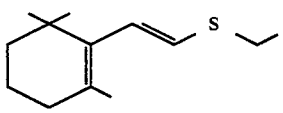

and the compound having the structure:

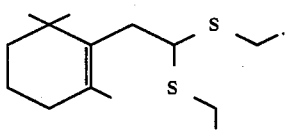

FIG. 8 is the GLC profile for the crude reaction product (Conditions: Carbowax column programmed at 100°–220° C. at 8° C. per minute). The peak indicated by reference numeral 81 is the peak for the compound having the structure:

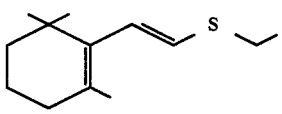

The peak indicated by reference numeral 82 is the peak for the compound having the structure:

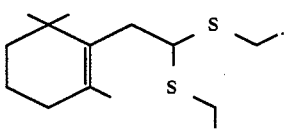

The compound having the structure:

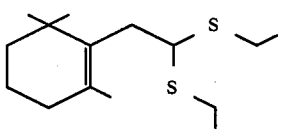

has a garlic and fried onion aroma and taste profile at 20 ppm causing it to be useful in onion soup flavored foodstuffs and garlic flavored foodstuffs. The compound having the structure:

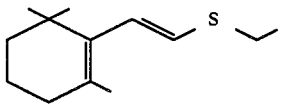

has a floral, green ad roasted aroma and taste profile at 0.5 ppm causing it to be useful in almond, roasted peanut and baked goods flavored foodstuffs.

FIG. 9 is the NMR spectrum for the compound having the structure:

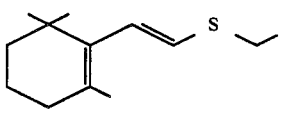

(Conditions: Field strength: 100 MHz; Solvent: CFCl$_3$).

FIG. 10 is the NMR spectrum for the peak indicated by reference numeral 82 for the compound having the structure:

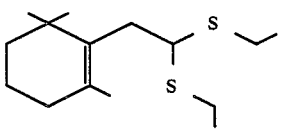

(Conditions: Field strength: 100 MHz; Solvent: CFCl$_3$).

EXAMPLE XVII

Preparation of 2,6,6,6-trimethyl-1-cyclohexene-1-acid Aldehyde Dipropyl Mercaptal and 1,3,3-trimethyl-2[2-(propylthio)ethenyl]cyclohexene Reaction:

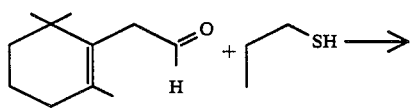

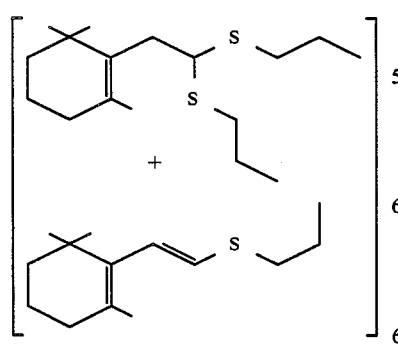

Into a Parr bomb equipped with stirrer is placed 10 grams of beta-homocyclocitral having the structure:

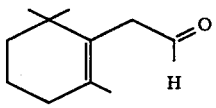

13.8 grams propyl mercaptan; 50 ml methylene dichloride and 0.1 grams of paratoluene sulfonic acid. The Parr bomb is sealed and heated with stirring to 110° C. The reaction mass is continued to be heated at 110° C. for a period of 7 hours. At the end of the 7 hour period, the Parr bomb contents are cooled and the Parr bomb is opened. The contents are washed with 2 volumes of 10% sodium carbonate solution followed by one 50 ml portion of water. The reaction mass is then dried over anhydrous sodium sulfate and the solvent is removed therefrom using a Buchi evaportor. The reaction mass is then distilled on a micro distillation column yielding the following fractions:

| Fraction No. | Vapor Temp. (0 C.) | Liquid Temp. (0 C.) | Vacuum mm/Hg. Pressure |
|---|---|---|---|
| 1 | /107 | 70 | 6 |
| 2 | 109 | 180 | 7 |
| 3 | 75 | 194 | 6 |
| 4 | 119 | 200 | 8 |
| 5 | — | 205 | 8 |

The resulting product is a mixture of two compounds having the structures:

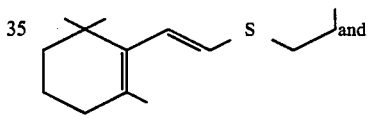

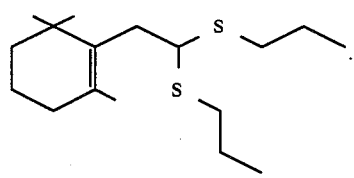

The compound having the structure:

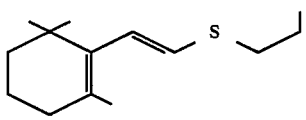

is separated from the compound having the structure:

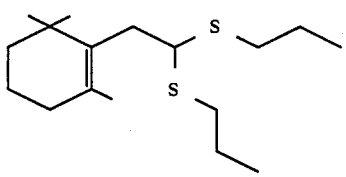

by means of preparative vapor phase chromatography. Fraction 2 contains primarily of a compound having the structure:

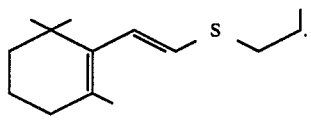

Fraction 5 is primarily the compound having the structure:

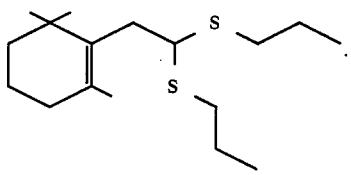

FIG. 11 is the GLC profile for the crude reaction product prior to distillation containing the compounds having the structures:

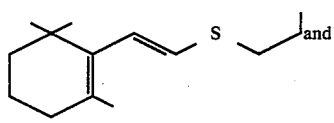

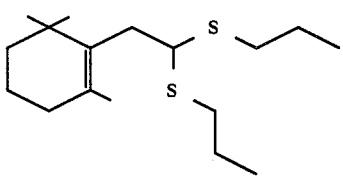

The peak indicated by reference numeral 111 is the peak for the compound having the structure:

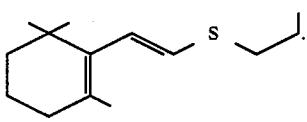

The peak indicated by reference numeral 112 is the peak for the compound having the structure:

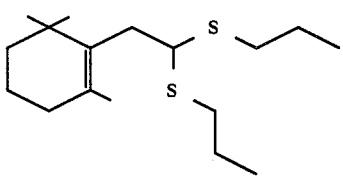

(GLC Conditions: Carbowax column programmed at 220° C. isothermal).

FIG. 12 is the NMR spectrum for the compound having the structure:

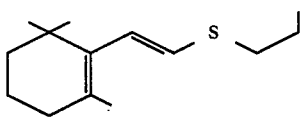

(Conditions: Field strength: 100 MHz; Solvent: CFCl$_3$).

FIG. 13 is the NMR spectrum for the compound having the structure:

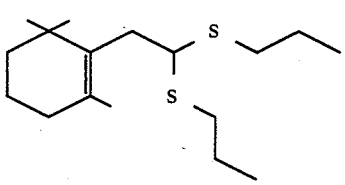

(Conditions: Field strength: 100 MHz; Solvent: CFCl$_3$).

The compound having the structure:

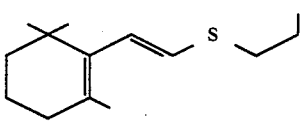

has a sweet, cherry, marachino cherry, oniony and bacon aroma and taste profile at 0.1 ppm causing it to be useful in cherry and black cherry foodstuffs. The compound having the structure:

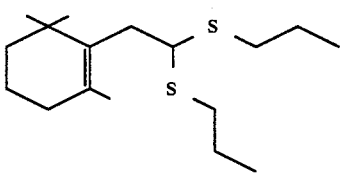

has an excellent onion, roasted, crisp roasted and bacon aroma and taste profile at 2 ppm causing it to be useful in bacon, roasted nut, roasted onion, almond and peanut flavored foodstuffs.

EXAMPLE XVIII(A)

Preparation of Onion Flavor Material

A mixture of 0.1 grams of the compound having the structure:

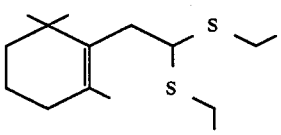

is admixed with 0.1 grams of methyl 1-propanethiosulfinate; 0.6 grams of propyl 1-propanethiosulfinate, and 0.3 grams of allyl 1-propanethiosulfinate. The resulting product is heated in a sealed vessel at 150° C. for 30 seconds. The thiosulfinates are partially converted to sulfides.

The resulting mixture has a very strong, freshly cooked onion aroma character with garlic and fried onion nuances.

EXAMPLE XVIII(B)

A half gram of the mixture of Example XVIII(A) is emulsified in a solution containing the following materials:

| Ingredients | Parts by Weight |
| --- | --- |
| Gum arabic | 100.0 |
| Water | 300.0 |
| Butylated hydroxy anisol (20% solution and ethanol) | 0.5 |

The resulting emulsion is spray dried in a Bowen Lab Model spray drier with the inlet temperature of 500° F. and outlet temperature of 200° F. 12 Grams of the spray-dried material is mixed with 29.2 grams of the following soup base:

| Ingredients | Parts by Weight |
| --- | --- |
| Fine ground sodium chloride | 35.62 |
| Hydrolyzed vegetable protein (Nestle 4 BE) | 27.40 |
| Monosodium glutamate | 17.81 |
| Sucrose | 10.96 |
| Beef fat | 5.48 |
| Sethness caramel color (powder B & C) | 2.73. |

The resulting mixture is then added to 12 ounces of boiling water and an excellent onion flavored soup with interesting, garlic and fried onion nuances is obtained. When the compound having the structure:

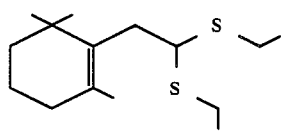

is replaced by the compound having the structure:

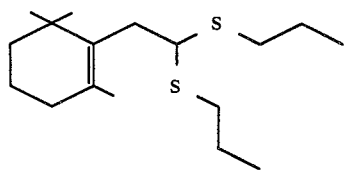

interesting onion, roasted, crisp-roasted and faint bacon nuances are obtained at one tenth of the level of use of the compound having the structure:

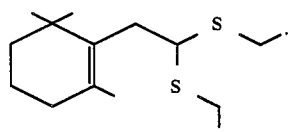

EXAMPLE XIX

A white bread dough mix is prepared by mixing 1350 gm wheat flour and 800 ml water. To the mix is added:

| Ingredients | Amount |
| --- | --- |
| Yeast | 27.00 |
| NaCl | 67.5 |
| Sucrose | 54.00 |
| Shortening | 40.5 |
| Non-fat dry milk powder | |

| Ingredients | Amount |
| --- | --- |
| Yeast food (Arkadv) manufactured by Fleischmann, Div. of Standard Brands | 0.50 |
| Softening agent (succinylated monoglycerides) manufactured by Kraft Div. of National Dairy Products Corporation | 3.4 |

Six grams of the compound having the structure:

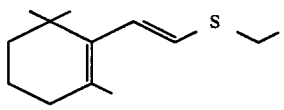

prepared according to Example XVII are added to the dough. The dough is then mixed for 8 minutes and allowed to rise for 45 minutes at 40° C.

The dough is then baked for 45 minutes at 210° C. The bread stuff product obtained has a flavor note reminiscent of the crust of home made Georgian bread with almond, roasted and peanut nuances and has acceptable and persistent flavor properties for a period of one week, and has good flavor characteristic when spread with margerine.

EXAMPLE XX

The compound having the structure:

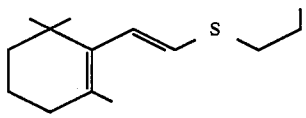

is added at the rate of 0.1 ppm to a standard marachino cherry flavor. The resulting marachino cherry flavor is added to blanched cherries at the rate of 5%. The resulting cherries have an excellent marachino cherry flavor with sweet, natural cherry nuances.

EXAMPLE XXI

Preparation of Dimethyl Mercaptal of Beta-Homocyclocitral

Reaction:

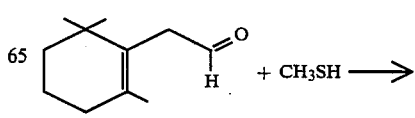

-continued

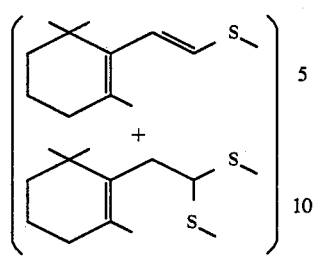

Into a 200 cc reaction vessel equipped with stirrer, thermometer, reflux condenser and cooling bath and gas addition tube are placed 16.4 grams beta-homocyclocitral having the structure:

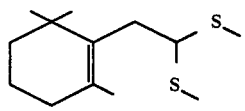

250 ml methylene dichloride; and 0.1 grams of paratoluene sulfonic acid.

Using a dry ice bath, the reaction mass is cooled with stirring to 0°–10° C. Over a period of 8 hours, 10 grams of methyl mercaptan is added through the addition funnel to the reaction flask. The reaction mass is then placed in a Parr bomb and sealed. The Parr bomb is heated with stirring to 110° C. and maintained at that temperature for a period of 8 hours. At the end of the 8 hour period, the Parr bomb is cooled and opened and the reaction mass is transferred to a separatory funnel and washed with two 50 ml portion of 10% sodium carbonate solution followed by one 50 ml portion of water. The reaction mass is then dried and distilled on a micro distillation apparatus, first recovery the solvent and then yielding the following fractions:

FIG. 14 is the GLC profile for the crude reaction product containing the compounds having the structures:

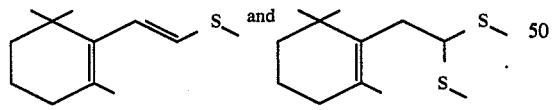

The peak indicated by reference numeral 140 is the peak for the methylene chloride. The peak indicated by reference numeral 141 is the peak for the beta-homocyclocitral having the structure:

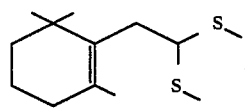

The peak indicated by reference numeral 142 is the peak for the compound having the structure:

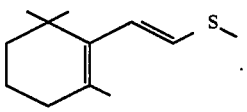

The peak indicated by reference numeral 143 is the peak for the compound having the structure:

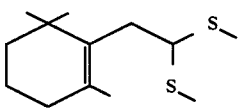

(Conditions: SE-30 column programmed at 100°–220° C. at 8° C. per minute).

FIG. 15 is the GLC profile for Fraction 5 of the foregoing distillation. The peak indicated by reference numeral 150 is the peak for the compound having the structure:

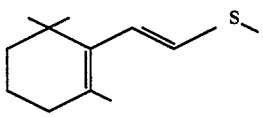

(Conditions: 8'×0.125" SE-30 column programmed at 100°–220° C. at 8° C. per minute).

FIG. 16 is the NMR spectrum for Fraction 5 of the foregoing distillation containing the compound having the structure:

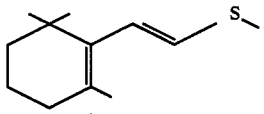

(Conditions: Field strength: 100 MHz; Solvent: CFCl₃).

FIG. 17 is the NMR spectrum of a purified version of Fraction 5 of the foregoing distillation containing the compound having the structure:

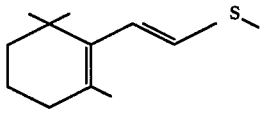

"Z":"E" ratio=2:1.

The compound having the structure:

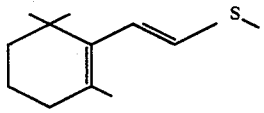

"Z":"E" ratio=2:1.

EXAMPLE XXII

The following peach flavor is prepared:

| Ingredient | Parts by Weight |
|---|---|
| Gamma-n-pentyl | 3.0 |

| Ingredient | Parts by Weight |
| --- | --- |
| The compound having the structure: 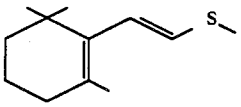 prepared according to Example XXI, distillation Fraction 5, 85% purity: "Z":"E" ratio = 2:1. | 6.0 |
| Amyl acetate | 15.0 |
| Amyl butyrate | 3.4 |
| Amyl formate | 6.8 |
| Amyl vallirate | 6.7 |
| Benzaldehyde | 4.2 |
| Benzylacetate | 2.1 |
| Bitter almond essence | 4.8 |
| Cinnamon | 0.1 |
| Ethyl acetate | 2.2 |
| Ethyl capronate | 18.4 |
| Gamma-undecalactone | 18.4 |
| Ethyl valorate | 7.3 |
| Orange, sweet, essential oil | 4.8 |
| Rum ether | 2.2 |
| Vanillan | 17.3 |
| Mandarin essential oil | 21.4 |
| Propylene glycol | q.s. |
| Vanillan | 17.3 |
| Mandarin essential oil | 21.4 |
| Propylene glycol | q.s. |

The resulting flavor is added at the rate of 100 ppm to GOYA ®NECTAR DEGUANABANA. The resulting Guanabana nectar has an excellent natural peach undertone causing it to be more aesthetically pleasing to a bench panel of five members (blind panel; not associated with inventive entity or assignee of instant application) over the same Guanabana nectar without the flavor or with the flavor, not containing the compound having the structure:

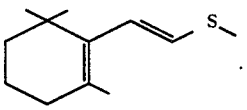

What is claimed is:

1. A process for augmenting or enhancing the aroma or taste of a foodstuff comprising the steps of intimately admixing with said foodstuff from about 0.001 ppm up to about 250 ppm of approximately 2:8 mixture of dithio derivatives having the structures:

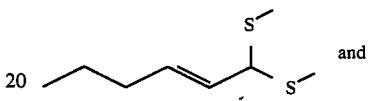 and

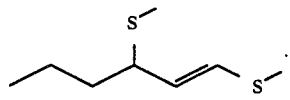

2. A process for augmenting or enhancing the aroma or taste of a foodstuff comprising the steps of intimately admixing with said foodstuff from about 0.001 ppm up to about 250 ppm of approximately 65:35 mixture of dithio derivation having the structures:

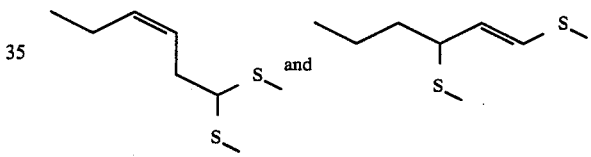

* * * * *